(12) United States Patent
Tsumura et al.

(10) Patent No.: US 7,847,931 B2
(45) Date of Patent: Dec. 7, 2010

(54) MEASURING EQUIPMENT

(75) Inventors: Naoki Tsumura, Kamiina-gun (JP); Kazushiro Fukushima, Nasushiobara (JP)

(73) Assignees: Tochigi Nikon Corporation, Otawara-shi (JP); Nikon Corporation, Tokyo (JP)

( * ) Notice: Subject to any disclaimer, the term of this patent is extended or adjusted under 35 U.S.C. 154(b) by 775 days.

(21) Appl. No.: 11/666,078

(22) PCT Filed: Nov. 1, 2005

(86) PCT No.: PCT/JP2005/020124

§ 371 (c)(1),
(2), (4) Date: Jun. 15, 2007

(87) PCT Pub. No.: WO2006/051728

PCT Pub. Date: May 18, 2006

(65) Prior Publication Data

US 2008/0013071 A1    Jan. 17, 2008

(30) Foreign Application Priority Data

Nov. 9, 2004  (JP) ............................. 2004-325264

(51) Int. Cl.
*G01J 3/00* (2006.01)
(52) U.S. Cl. .................................... 356/300
(58) Field of Classification Search .................. 356/51, 356/317, 450, 432, 484; 250/330
See application file for complete search history.

(56) References Cited

U.S. PATENT DOCUMENTS 6,747,736 B2   6/2004  Takahashi

2001/0029436 A1   10/2001  Fukasawa
2002/0005951 A1 *  1/2002  Fukasawa .................... 356/432

(Continued)

FOREIGN PATENT DOCUMENTS

EP           1 469 298 A1    10/2004

(Continued)

OTHER PUBLICATIONS

Daniel F. Filipovic et al., "Double-Slot Antennas on Extended Hemispherical and Elliptical Silicon Dielectric Lenses," IEEE Transactions on Microwave Theory and Techniques, vol. 41, No. 10, Oct. 1993, pp. 1738-1749, Section VII.

(Continued)

*Primary Examiner*—Tarifur Chowdhury
*Assistant Examiner*—Abdullahi Nur
(74) *Attorney, Agent, or Firm*—Oliff & Berridge, PLC

(57) ABSTRACT

A measuring equipment utilizing terahertz pulse light, includes: a terahertz light generator that generates terahertz pulse light; a terahertz light detector that detects terahertz pulse light; a first condensing optical system that condenses the terahertz pulse light generated by the terahertz light generator; and a second condensing optical system that condenses the terahertz pulse light diverging after being condensed by the first condensing optical system, onto the terahertz light detector. A sample is arranged in a vicinity of a position of condensing the terahertz pulse light by the first condensing optical system; and at least one of the first and the second condensing optical systems includes at least one optical device having a positive or negative refractive power. The measuring equipment further includes: a position adjusting mechanism that adjusts a position of the at least one optical device on an optical axis when the terahertz light detector detects the terahertz pulse light having transmitted through the sample; and a controlling unit that controls the position adjusting mechanism.

13 Claims, 16 Drawing Sheets

U.S. PATENT DOCUMENTS

| | | |
|---|---|---|
| 2002/0067480 A1 | 6/2002 | Takahashi |
| 2004/0246493 A1* | 12/2004 | Kim et al. .................. 356/504 |
| 2005/0082479 A1 | 4/2005 | Wallace et al. |

FOREIGN PATENT DOCUMENTS

| | | |
|---|---|---|
| JP | A 2001-50908 | 2/2001 |
| JP | A 2003-75251 | 3/2003 |
| JP | A 2004-212110 | 7/2004 |
| WO | WO 00/79248 A1 | 12/2000 |
| WO | WO 03/023383 A3 | 3/2003 |
| WO | WO 03/095991 A1 | 11/2003 |

OTHER PUBLICATIONS

Supplementary European Search Report issued May 11, 2010 for European Application No. EP 05 80 5481.8.

* cited by examiner

FOURTH MEASURING MODE (REFERENCE MEASUREMENT WITH SAMPLE, WHEN REFRACTIVE INDEX OF SAMPLE IS UNKNOWN AND REFRACTIVE INDEX OF REFERENCE SAMPLE IS KNOWN)

SEVENTH MEASURING MODE (REFERENCE MEASUREMENT WITH REFERENCE SAMPLE)

MEASURING EQUIPMENT

TECHNICAL FIELD

The present invention relates to measuring equipment utilizing terahertz light such as a terahertz spectral instrument.

BACKGROUND ART

Hitherto, there has been provided a measuring equipment including a first condensing optical system for condensing terahertz pulse light generated by a terahertz light generator, a second condensing optical system for condensing terahertz pulse light diverging after being condensed through the first condensing optical system to the terahertz light detector, wherein a sample is arranged in the vicinity of the condensing position of terahertz pulse light by the first condensing optical system and the terahertz pulse light that has transmitted through the sample is detected by the terahertz light detector (for example, Patent Documents 1 and 2 described below).

In such conventional measuring equipment, as disclosed in Patent Documents 1 and 2, the first condensing optical system includes a first parabolic mirror for converting terahertz pulse light generated by the terahertz light generator into parallel beam and a second parabolic mirror for condensing the parallel beam to a focal point. The second condensing optical system includes a third parabolic mirror for converting the terahertz pulse light diverging after being condensed through the second condensing optical system into a parallel beam and a fourth parabolic mirror for condensing the parallel beam to the terahertz light detector. Then, upon production of the equipment, the terahertz light generator is arranged at the focal point of the first parabolic mirror and the terahertz light detector is arranged at the focal point of the fourth parabolic mirror, the positional relationship among these being fixed. That is, the conventional equipment is set such that when no sample is charged, the terahertz pulse light is condensed in an effective light receiving region of the terahertz light detector in the best focused state.

As just described, it is common for a measuring equipment utilizing terahertz light, such as a terahertz spectroscopic instrument, to use the above-mentioned first and second condensing optical systems when transmission measurement is performed in a small region of a sample. This is because terahertz light has a long wavelength (for example, the wavelength is about 300 µm at a frequency of 1 THz), so that there occurs a high diffraction effect and parallel beam of terahertz light with a small diameter can not be made.

Patent Document 1: Japanese Patent Application Laid-Open No. 2003-75251
Patent Document 2: Japanese Patent Application Laid-Open No. 2004-212110

DISCLOSURE OF THE INVENTION

Problems to be Solved by the Invention

However, in the above-mentioned measuring equipment, it revealed that when a sample is arranged in the vicinity of the condensing position of the first condensing optical system, the condensing state of terahertz pulse light to the terahertz light detector is decreased due to the thickness and the refractive index of the sample, causing so-called blurring.

Here, FIG. 1 schematically illustrates the state of terahertz pulse light in the vicinity of a second and a third parabolic mirrors 102, 103 in the above-mentioned conventional measuring equipment when a sample 100 is absent. FIG. 2 schematically illustrates the state of terahertz pulse light in the vicinity of the second and the third parabolic mirrors 102, 103 in the above-mentioned conventional measuring equipment when a sample 100 is arranged. To facilitate comparison of the both, FIG. 2 indicates in broken line the state of terahertz pulse state after point A in FIG. 1.

As illustrated in FIGS. 1 and 2, the terahertz pulse light in parallel beam from the first parabolic mirror (not shown) enters the second parabolic mirror 102 and is reflected by the parabolic mirror 102 to be condensed to the point A in FIGS. 1 and 2. The point A designates a focal point of the second parabolic mirror 102 and corresponds to a focal point of the third parabolic mirror 103.

When the sample 100 is absent as illustrated in FIG. 1, the terahertz pulse light condensed to the point A enters the third parabolic mirror 103 as a diverging beam emitted from the point A and is reflected by the third parabolic mirror 103 to give a parallel beam. The parallel beam is reflected by the fourth parabolic mirror (not shown) and is ideally condensed to the terahertz light detector (not shown) arranged at the focal point of the fourth parabolic mirror.

On the other hand, when the sample 100 is arranged in the vicinity of the point A as illustrated in FIG. 2 (in the example shown in FIG. 2, the sample 100 is arranged such that the front side thereof conforms to the point A), the terahertz pulse light reflected on the second parabolic mirror 102 is refracted by the sample 100, so that the terahertz pulse light that transmitted the sample 100 apparently becomes the same diverging beam as diverging beam emitted from a point B which is off the point A and incident to the third parabolic mirror 103. Since the point B is off the point A (the focal point of the third parabolic mirror 103), the terahertz pulse light reflected by the parabolic mirror 103 does not form parallel beam. Therefore, the terahertz pulse light reflected thereafter by the fourth parabolic mirror can not be ideally condensed to the focal point of the fourth parabolic mirror, resulting in a decrease in the condensation state of the terahertz pulse light to the terahertz light detector arranged at the focal point of the fourth parabolic mirror, thus causing so-called blurring.

As a result, an incidence state of terahertz pulse light to an effective receiving region of the terahertz detector changes depending on whether or not a sample is arranged. On this occasion, different wavelength components of the terahertz pulse light show different changes in the incidence state. This tendency increases when a detector with a small effective light receiving region, such as a light transmission antenna using a dipole antenna is used as a terahertz light detector.

Therefore, in the above-mentioned conventional measuring equipment, a change in condensation state of terahertz pulse light to the terahertz light detector may lead to a decrease in an SN ratio or a deviation of the spectroscopic characterization obtained by measurement from the original spectral characterization. This increases measurement errors in the above-mentioned conventional measuring equipment due to the thickness and the refractive index of the sample.

For example, when spectroscopic measurement is performed, generally, blurring due to the thickness and the refractive index of a sample is a major cause of measurement errors since a detected signal obtained in a state where the sample is arranged is compared with a detected signal obtained in a state where no sample is arranged (reference signal). In addition, when spectroscopic measurement is performed, the detected signal obtained in the state where the sample is arranged may be compared with a detected signal obtained in a state where a reference sample (for example, a glass plate or the like) instead of the sample is arranged. In this case too, differences in thickness and refractive index between the sample as an original subject of measurement and the reference sample will lead to a change in a state of incidence of terahertz pulse light to the effective light receiving region of the terahertz detector depending whether the original sample is arranged or the reference sample is arranged. Therefore, when spectroscopic measurement is performed using the reference sample, measurement errors increase due to the thickness and the refractive index of the sample.

Means for Solving the Problems

According to the 1st aspect of the present invention, a measuring equipment utilizing terahertz pulse light, comprises: a terahertz light generator that generates terahertz pulse light; a terahertz light detector that detects terahertz pulse light; a first condensing optical system that condenses the terahertz pulse light generated by the terahertz light generator; and a second condensing optical system that condenses the terahertz pulse light diverging after being condensed by the first condensing optical system, onto the terahertz light detector. A sample is arranged in a vicinity of a position of condensing the terahertz pulse light by the first condensing optical system; and at least one of the first and the second condensing optical systems includes at least one optical device having a positive or negative refractive power. The measuring equipment further comprises: a position adjusting mechanism that adjusts a position of the at least one optical device on an optical axis when the terahertz light detector detects the terahertz pulse light having transmitted through the sample; and a controlling unit that controls the position adjusting mechanism.

According to the 2nd aspect of the present invention, in the measuring equipment according to the 1st aspect, it is preferred that the controlling unit controls the position adjusting mechanism in a direction such that the terahertz pulse light having transmitted through the sample is focused onto the terahertz light detector.

According to the 3rd aspect of the present invention, in the measuring equipment according to the 1st or 2nd aspect, it is preferred that the controlling unit controls the position adjusting mechanism depending on a thickness and a refractive index of the sample.

According to the 4th aspect of the present invention, in the measuring equipment according to any one of the 1st to 3rd aspect, it is preferred that the controlling unit controls the position adjusting mechanism so that a focused state of the terahertz pulse light having transmitted through the sample to the terahertz light detector is the same as a focused state of the terahertz pulse light to the terahertz light detector when no sample is arranged.

According to the 5th aspect of the present invention, in the measuring equipment according to the 1st aspect, it is preferred that: the terahertz light generator generates the terahertz pulse light in response to pump pulse light incident to the terahertz light generator; the terahertz light detector detects the terahertz pulse light in response to probe pulse light incident to the terahertz light generator; and there is further provided a light path length altering unit that alters a light path length of the pump pulse light and a light path length of the probe pulse light relative to each other.

According to the 6th aspect of the present invention, in the measuring equipment according to any one of the 2nd to 4th aspects, it is preferred that: the terahertz light generator generates the terahertz pulse light in response to pump pulse light incident to the terahertz light generator; the terahertz light detector detects the terahertz pulse light in response to probe pulse light incident to the terahertz light generator; and there is further provided a light path length altering unit that alters a light path length of the pump pulse light and a light path length of the probe pulse light relative to each other.

According to the 7th aspect of the present invention, in the measuring equipment according to the 6th aspect, it is preferred that there are further provided: a first time-series waveform obtaining unit that obtains a time-series waveform of electric field intensity of terahertz pulse light incident to the terahertz light detector based on a detected signal from the terahertz light detector, the detected signal being obtained by relatively altering the light path length of the pump pulse light and the light path length of the probe pulse light by the light path length altering unit in a state where the sample is absent; a second time-series waveform obtaining unit that obtains a time-series waveform of electric field intensity of terahertz pulse light incident to the terahertz light detector based on a detected signal from the terahertz light detector, the detected signal being obtained by relatively altering the light path length of the pump pulse light and the light path length of the probe pulse light by the light path length altering unit in a state where the sample is arranged in the vicinity of a condensing position at which the terahertz pulse light is condensed by the first condensing optical system; and a calculating unit that calculates a moving amount of the at least one optical device based on a time difference between a peak of a time-series waveform obtained by the first time-series waveform obtaining unit and a peak of a time-series waveform obtained by the second time-series waveform obtaining unit, the controlling unit controlling the position adjusting mechanism based on the moving amount obtained by the calculating unit.

According to the 8th aspect of the present invention, in the measuring equipment according to the 6th aspect, it is preferred that there are further provided: a first time-series waveform obtaining unit that obtains a time-series waveform of electric field intensity of terahertz pulse light incident to the terahertz light detector based on a detected signal from the terahertz light detector, the detected signal being obtained by relatively altering the light path length of the pump pulse light and the light path length of the probe pulse light by the light path length altering unit in a state where a reference sample instead of the sample is arranged in the vicinity of a condensing position at which the terahertz pulse light is condensed by the first condensing optical system; a second time-series waveform obtaining unit that obtains a time-series waveform of electric field intensity of terahertz pulse light incident to the terahertz light detector based on a detected signal from the terahertz light detector, the detected signal being obtained by relatively altering the light path length of the pump pulse light and the light path length of the probe pulse light by the light path length altering unit in a state where the sample is arranged in the vicinity of a condensing position at which the terahertz pulse light is condensed by the first condensing optical system; and a calculating unit that calculates a moving amount of the at least one optical device based on a time difference between a peak of a time-series waveform obtained by the first time-series waveform obtaining unit and a peak of a time-series waveform obtained by the second time-series waveform obtaining unit, and the controlling unit controlling the position adjusting mechanism based on the moving amount obtained by the calculating unit.

According to the 9th aspect of the present invention, in the measuring equipment according to the 5th aspect, it is preferred that the controlling unit (i) monitors a detected signal from the terahertz light detector obtained by relatively altering the light path length of the light path of the pump pulse light and the light path length of the light path of the probe pulse light by the light path length altering unit in a state where the sample is arranged in the vicinity of a condensing position at which the terahertz pulse light is condensed by the first condensing optical system, and fixes the light path length of each light path based on the result of the monitoring so that the detected signal becomes maximum; (ii) and monitors, in the fixed state, a detected signal from the terahertz light detector obtained by moving the optical device by the position adjusting mechanism, and controls the position adjusting mechanism so that the optical device is positioned at a position at which the detected signal is maximum.

According to the 10th aspect of the present invention, in the measuring equipment according to the 3rd aspect, it is preferred that the controlling unit calculates an offset amount between a diverging point of terahertz pulse light that diverges without being transmitted through the sample after being condensed by the first condensing optical system and a diverging point of terahertz pulse light having transmitted through the sample after being condensed by the first condensing optical system and diverging based on a thickness and a refractive index of the sample and controls the position adjusting mechanism based on the calculated offset amount.

According to the 11th aspect of the present invention, in the measuring equipment according to the 1st aspect, it is preferred that the controlling unit controls the position adjusting mechanism, so that a rear focal point of the first condensing optical system coincides with a front focal point of the second condensing optical system either when the sample is present or when the sample is absent.

According to the 12th aspect of the present invention, in the measuring equipment according to the 1st aspect, it is preferred that: the controlling unit controls the position adjusting mechanism, so that when the sample is not in the vicinity of the condensing position, the at least one optical device is positioned at a first predetermined position, and when the sample is in the vicinity of the condensing position, the at least one optical device is positioned at a second position offset from the first position; the terahertz light detector detects the terahertz pulse light in a state where the sample is not in the vicinity of the condensing position and in a state where the at least one optical device is positioned at the first position to output a first detection result, and detects the terahertz pulse light in a state where the sample is in the vicinity of the condensing position and in as state where the at least one optical device is positioned at the second position to output a second detection result; and there is further provided a spectroscopic data generating unit that generates spectroscopic data of the sample based on the first and the second detection results.

According to the 13th aspect of the present invention, in the measuring equipment according to the 1st aspect, it is preferred that: the controlling unit controls the position adjusting mechanism, so that when the sample is not in the vicinity of the condensing position, the at least one optical device is positioned at a first predetermined position, and when the sample is in the vicinity of the condensing position, the at least one optical device is positioned at a second position offset from the first position, and when a reference sample is in the vicinity of the condensing position, the at least one optical device is positioned at a third position offset from the first position; the terahertz light detector detects the terahertz pulse light in a state where the reference sample is in the vicinity of the condensing position and in a state where the at least one optical device is positioned at the third position to output a first detection result, and detects the terahertz pulse light in a state where the sample is in the vicinity of the condensing position and in a state where the at least one optical device is positioned at the second position to output a second detection result; and there is further provided a spectroscopic data generating unit that generates spectroscopic data of the sample based on the first and the second detection results.

According to the 14th aspect of the present invention, in the measuring equipment according to the 12th aspect, it is preferred that the controlling unit obtains an offset amount of the second position from the first position based on a thickness and a refractive index of the sample.

According to the 15th aspect of the present invention, in the measuring equipment according to the 13th aspect, it is preferred that the controlling unit obtains an offset amount of the second position from the first position based on a thickness and a refractive index of the sample and an offset amount of the third position from the first position based on a thickness and a refractive index of the reference sample.

The terahertz light generator may be replaced by terahertz light generating means; the terahertz light detector may be replaced by terahertz light detecting means; the first condensing optical system may be replaced by first condensing optical system means; the second condensing optical system may be replaced by second condensing optical system means; control unit may be replaced by control means; the light path length varying unit may be changed by light path length varying means; the first time-series waveform procuring unit may be replaced by first time-series waveform procuring means; the second time-series waveform procuring unit may be replaced by second time-series waveform procuring means; the calculating unit may be replaced by calculating means; and spectroscopic data generating unit may be replaced by spectroscopic data generating means.

ADVANTAGEOUS EFFECTS OF THE INVENTION

According to the present invention, measurement errors due to the thickness and the refractive index of a sample can be decreased.

BEST MODE FOR CARRYING OUT THE INVENTION

Hereinafter, the measuring equipment according to the present invention is described with reference to the attached drawings.

First Embodiment

Figure 2:
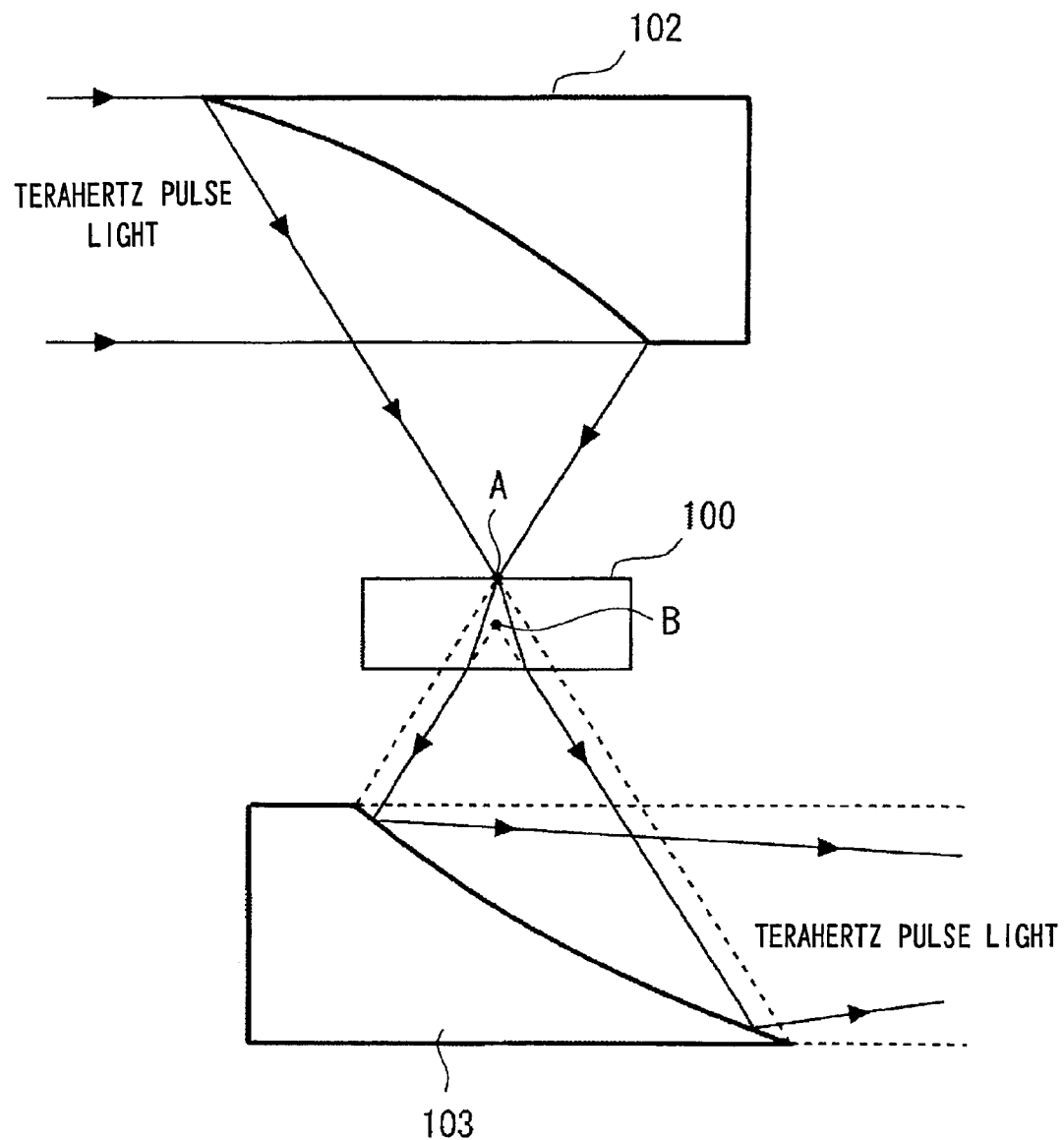
FIG. 2 is a schematic diagram illustrating the state of terahertz pulse light in the vicinity of the second and the third parabolic mirrors in a conventional measuring equipment when a sample is arranged.
Figure 3:
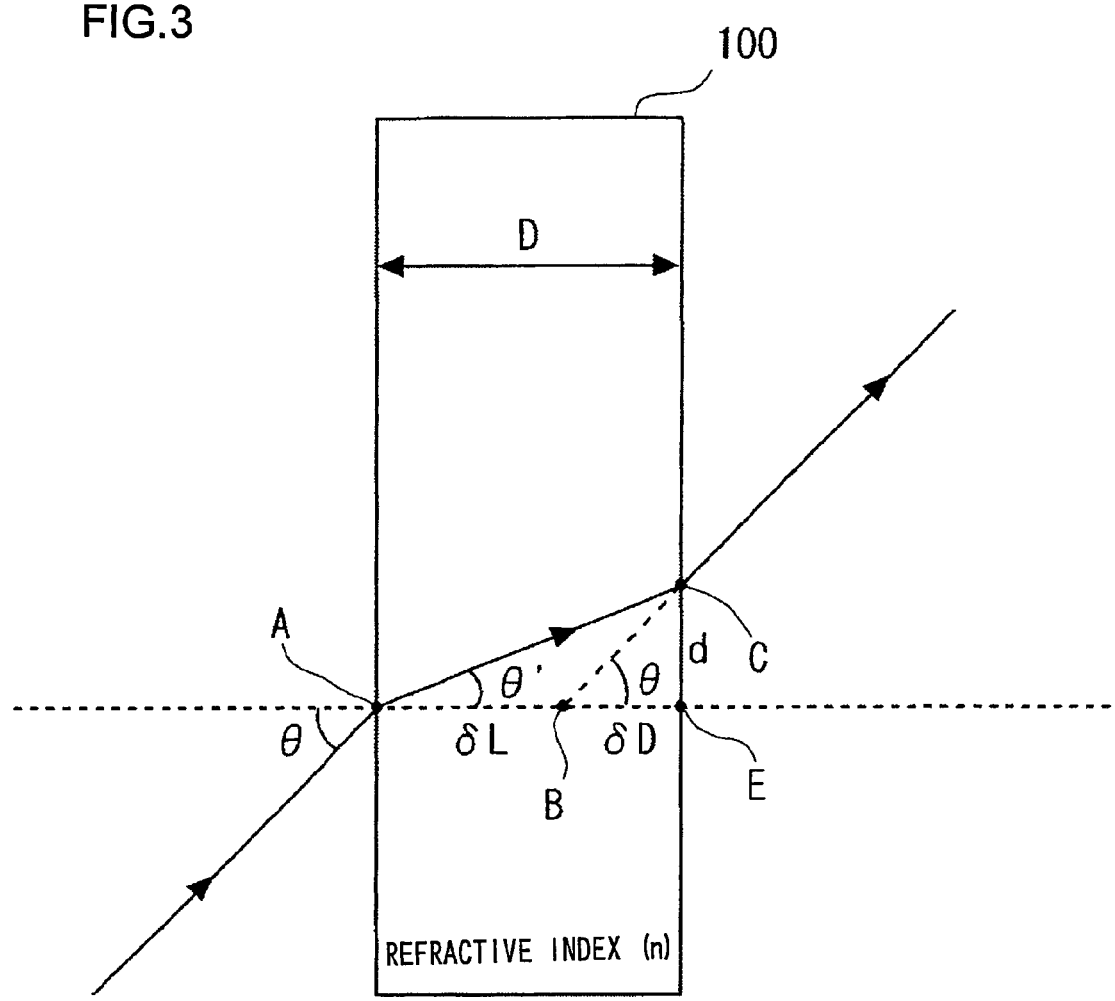
FIG. 3 is a diagram illustrating the state of beam of terahertz pulse light in the vicinity of the sample in FIG. 2.

Prior to description of the first embodiment of the present invention, referring to FIG. 3, how to obtain $\delta L$, a distance between points A and B (an offset amount between the points A and B) in FIG. 2 is described in order to facilitate understanding of the principle of decreasing measurement errors in the present embodiment. FIG. 3 is a diagram illustrating the state of beam of terahertz pulse light in the vicinity of the sample 100 in FIG. 2. As will be understood from the above-mentioned description, the point A represents a divergence point of diverging beam of the terahertz pulse light incident to the third parabolic mirror 103 when no sample 100 is arranged. The point B represents an apparent divergence point of diverging beam of the terahertz pulse light incident to the third parabolic mirror 103 (transmitted light having passed through the sample 100) when the sample 100 is arranged.

Now, assume that as shown in FIG. 3, the sample 100 is arranged in vacuum, the sample 100 has a refractive index n and a thickness of D. Then, suppose beam incident to the sample 100 from the point A at an incidence angle $\theta$. The beam is refracted at the point A and then outgoes from the sample 100 at the point C. Assume as shown in FIG. 3, a point on an optical axis on the plane at the backside of the sample 100 is E, $\angle BAC$ is $\theta'$, the distance between the points B and E is $\delta D$, and the distance between the points C and E is d. The points A and B are on the light axis. Then, by the Snell's law, $\angle CBE = \theta$.

As will be understood from FIG. 3, an offset amount $\delta L$ is given by the following equation 1.

$\delta L = D - \delta D$ (Equation 1)

The distance d in FIG. 2 is expressed by the following equations 2 and 3. From the equations 2 and 3, $\delta D$ is given by the following equation 4.

$\delta D \tan \theta = d$ (Equation 2)

$D \tan \theta' = d$ (Equation 3)

$\delta D = D(\tan \theta'/\tan \theta) = D(\sin \theta' \cdot \cos \theta)/(\sin \theta \cdot \cos \theta')$ (Equation 4)

According to the Snell's law, the following equation 5 is obtained.

$\sin \theta' = (\sin \theta)/n$ (Equation 5)

Substitution of the equations 4 and 5 in the equation 1 yields the following equation 6. In the equation 6, at a limit of $\theta \to 0$, the offset amount $\delta L$ is as expressed by the following equation 7.

$\delta L = D(1 - (1/n) \cdot (\cos \theta / \cos \theta'))$ (Equation 6)

$\delta L = D(1 - 1/n)$ (Equation 7)

In the examples shown in FIGS. 2 and 3, the sample 100 is arranged such that the surface at the front side conforms to the point A. However, if the sample 100 is offset from the position to and fro, the equation 7 is valid as is.

Generalizing the above, it can be seen that in a situation where terahertz pulse light condensed into diverging beam, an offset amount between the diverging point A of the diverging beam when no sample 100 is arranged and the apparent diverging point B where of the diverging beam when the sample 100 is arranged in the vicinity of the condensing position is given by the equation 7.

Figure 4:
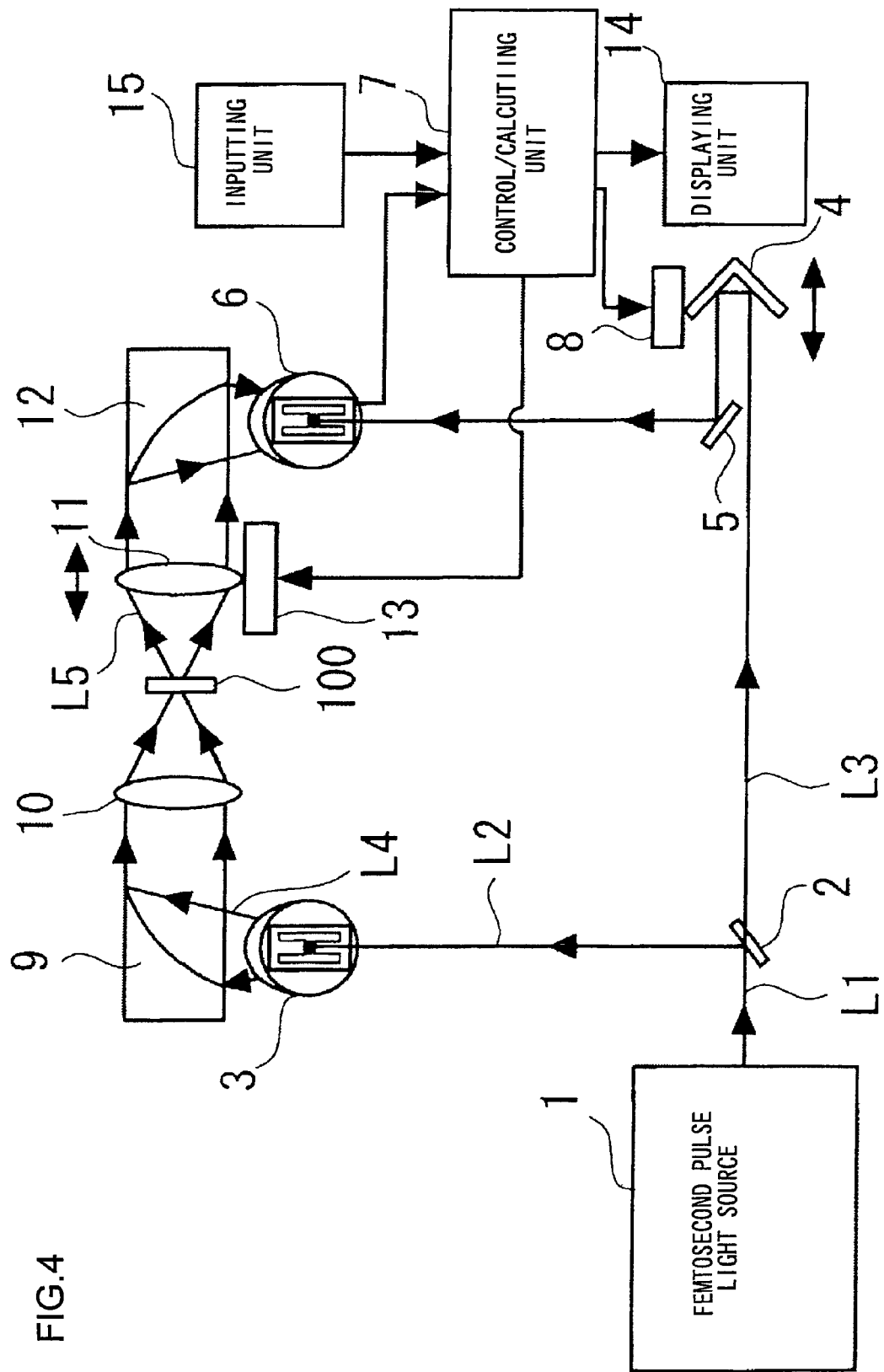
FIG. 4 is a schematic configuration diagram schematically illustrating measuring equipment according to a first embodiment of the present invention.

FIG. 4 is a schematic configuration diagram schematically illustrating the measuring equipment (apparatus) of the first embodiment of the present invention.

The measuring equipment according to the present embodiment is configured as a terahertz spectroscopic apparatus, in particular a time-series conversion terahertz spectroscopic apparatus. With the time-series conversion terahertz spectroscopic apparatus, the spectroscopic characterization of a sample is measured by measuring the time-series wave form of electric field of terahertz pulse light that passed through the sample and subjecting the obtained time-series waveform to Fourier transformation.

In the measuring equipment according to the present embodiment, as shown in FIG. 4, femtosecond pulse light L1 from a femtosecond pulse light source 1 is split by a beam splitter 2 into two beams of pulse light L2 and L3.

One of the two beams of pulse light being split by the beam splitter 2, L2, provides pump pulse light (pulse excitation light) that excites the terahertz light generator, such as an optical switch device for a photoconductive antenna using, e.g., a dipole antenna, or an EO crystal to generate terahertz pulse light in the generator 3. The pump pulse light L2 is guided to the terahertz light generator 3 to radiate terahertz pulse light L4. When an optical switch device is used as the terahertz light generator 3, a bias voltage is applied to the terahertz light generator 3 from a bias battery (not shown).

The other pulse light L3 being split by the beam splitter 2 provides probe pulse light that determines timing of detecting terahertz pulse light. The probe pulse light L3 is guided through a movable mirror 4 including a combination of two or three plane mirrors and further a plane mirror 5 to a terahertz light detector 6. In the present embodiment, an optical switch device with a dipole antenna is used as the terahertz light detector. However, the present invention should not be limited thereto.

The movable mirror 4 arranged on the light path of the probe pulse light L3 is movable in a lateral direction in FIG. 4 by a stage 8 as a moving mechanism for altering the light path length under control by a control/calculation unit 7. In response to the amount of translation of the movable mirror 4, the light path length of the probe pulse light L3 is altered, so that the time in which the probe pulse light L3 reaches the terahertz light detector 6 is delayed. That is, in the present embodiment, the movable mirror 4 and the light path length altering stage (delay stage) 8 constitute a light path length altering unit that can alter the light path length of the probe pulse light L3 relative to the light path length of the pump pulse light L2. The generation of the terahertz pulse light by the terahertz light generator 3 needs to be in synchronization with timing in which the probe pulse light L3 reaches the terahertz light detector 6. Further, to obtain a time-series waveform of terahertz pulse light by a so-called pump-probe method, the timing of the probe pulse light L3 in the period of time in which the terahertz pulse light generated by the terahertz light generator 3 has reached the terahertz light detector 6 needs to be altered. For this purpose, in the present embodiment, the light path length altering unit is provided.

The terahertz pulse light L4 generated by the terahertz light generator 3 is preferably light in a frequency range of approximately $0.1 \times 10^{12}$ to $100 \times 10^{12}$. The terahertz pulse light L4 is condensed to the condensing position through a parabolic mirror 9 and a condensing lens 10 as an optical device having a positive refractive power (a transmissive optical device in the present embodiment). The parabolic mirror 9 converts the terahertz pulse light L4 into a parallel beam and the condensing lens 10 condenses the terahertz pulse light L4 converted into a parallel beam at its focal point.

In the present embodiment, the parabolic mirror 9 and the condensing lens 10 constitutes a first condensing optical system for condensing the terahertz pulse light generated by the terahertz light generator. In the vicinity of the focal point of the condensing lens 10, a measurement portion for a sample 100 as a subject to be measured is arranged. However, when performing the reference measurement described hereinbelow, the sample 100 may not be arranged or a reference sample (not shown) may be arranged.

The terahertz pulse light L5 having transmitted through the sample 100 becomes a diverging beam first, and then is converted into a parallel beam by a condensing lens 11 as a transmissive optical device having a positive refractive power and further condensed to an effective light receiving region of the terahertz light detector 6 by a parabolic mirror 12. In the present embodiment, the condensing lens 11 and the parabolic mirror 12 constitutes a second condensing optical system that allows the terahertz pulse light L5 diverging after being condensed through the first condensing optical system to condense onto the terahertz light detector 6.

Examples of the material constituting the transmissive optical device included in the first and second condensing optical systems (i.e., condensing lenses 10, 11 in the present embodiment) include polyethylene, polymethylpentene, quartz, sapphire, silicon, gallium arsenide, MgO, Ge, and diamond. The materials are preferred since they have relatively high transmittance for terahertz pulse light.

In the present embodiment, a stage 13 is provided as a position adjusting mechanism for adjusting the position of the condensing lens 11 on the optical axis. As described in detail hereinbelow, in the present embodiment, the terahertz pulse light L5 having transmitted through the condensing lens 11 always becomes a substantially parallel beam regardless of whether the sample 100 is arranged, no sample 100 is arranged, or a reference sample instead of the sample 100 is arranged by adjusting the position of the condensing lens 11 on the optical axis under control of the control/calculation unit 7. This prevents the condensation state of the terahertz pulse light L5 to the terahertz light detector 6 from being decreased, thus causing no blurring.

The terahertz pulse light 15 condensed to the terahertz light detector 6 is detected by the terahertz light detector 6 to be converted into an electrical signal. The electrical signal is fed to the control/calculation unit 7 including an amplifier, an A/D converter, and a computer and so on and is stored in an internal memory as a detected signal for electric field intensity of the terahertz pulse light after amplification, A/D conversion and so on.

The recurrence period of femtosecond pulse light L1 radiated from the femtosecond pulse light source 1 is on the order of a few kHz to 100 MHz. Therefore, the terahertz pulse light L4 to be radiated from the terahertz light generator 3 is radiated in a recurrence period on the order of a few kHz to 100 MHz. Current terahertz light detector 6 can not measure the waveform of the terahertz pulse light instantaneously as it is.

Therefore, in the present embodiment, a so-called pump-probe method is adopted in which utilizing the fact that the terahertz pulse light L5 having the same waveform arrives in a recurrence period on the order of a few kHz to 100 MHz, the waveform of the terahertz pulse light L5 is measured with a delay time being provided between the pump pulse light L2 and the probe pulse light L3.

That is, the timing in which the terahertz light detector 6 is activated by the probe pulse light is delayed by time $\tau$ relative to the timing in which the terahertz pulse light generated by the terahertz light generator 3 activated by the pump pulse light L2 reaches the terahertz light detector 6. This enables the terahertz light detector 6 to measure the electric field intensity of the terahertz pulse light L5 at a point in time which is delayed by time $\tau$.

In other words, the probe light L3 provides the terahertz light detector 6 with a gate. Moving the movable mirror 4 gradually is nothing other than changing the delay time $\tau$ gradually. The time-series waveform $E(\tau)$ of the electric field intensity of the terahertz pulse light L5 can be measured by shifting timing at which a gate is provided by the light path length altering unit and sequentially obtaining an electric field intensity of each recurrently arriving terahertz pulse light L5 at timing with each delay time as electrical signal.

In the present embodiment, upon measuring the time-series waveform $E(\tau)$ of the electric field intensity of the terahertz pulse light, the control/calculation unit 7 sends a control signal to the stage 8 to gradually alter the delay time $\tau$ and sequentially store data obtained by amplifying and A/D converting the electrical signals from the terahertz light detector 6 in a memory (not shown) in the control/calculation unit 7. This allows the whole data representing the time-series waveform $E(\tau)$ of the electric field intensity of the terahertz pulse light L5 to be stored in the memory. Such data representing the time-series waveform $E(\tau)$ is obtained for each of the cases where the sample 100 is arranged in the position shown in FIG. 4, where no sample 100 is arranged, or where a reference sample (for example, a glass plate or the like) instead of the sample 100 is arranged. The control/calculation unit 7 obtains the spectroscopic data of the sample 100 based on the above-mentioned data and the obtained data is displayed on a displaying unit 14 such as a liquid crystal panel or a CRT.

In the present embodiment, the control/calculation unit 7, based on instruction from an inputting unit 15 including a keyboard or other operation devices, realizes operations of a first to a fifth measuring modes shown in FIGS. 5 to 9, respectively. However, in the present invention, the control/calculation unit 7 may be configured to realize only any one of or two or more measuring modes out of the first to the fifth measuring modes.

Figure 5:
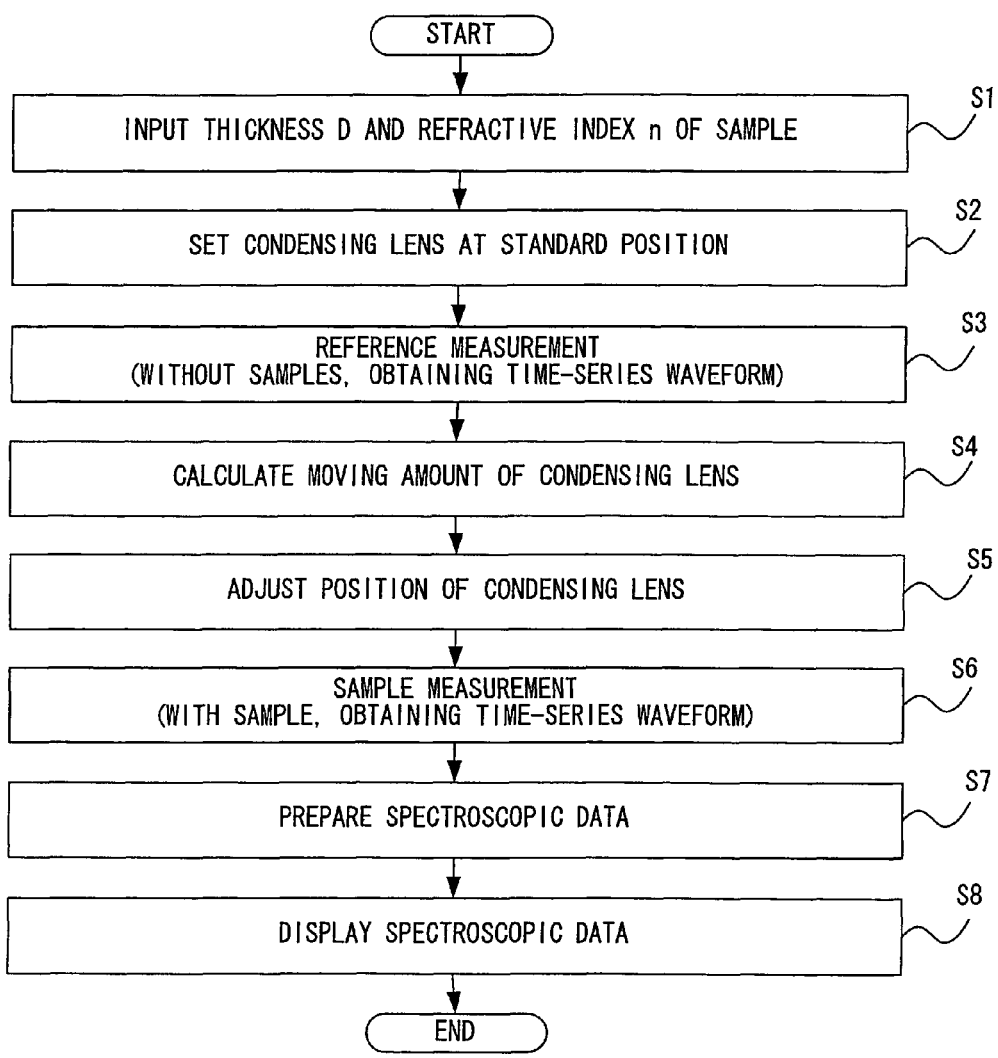
FIG. 5 is a schematic flowchart illustrating an operation in a first measuring mode of the measuring equipment according to the first embodiment of the present invention.

The first measuring mode is a measuring mode in which reference measurement is performed in a state where no sample 100 is present (in a state where nothing is arranged between the condensing lenses 10 and 11) and the spectroscopic data of the sample 100 is obtained when the refractive index n of the sample 100 is known. FIG. 5 is a schematic flowchart illustrating operation of the first measuring mode.

The control/calculation unit 7, when given instruction for the first measuring mode by the inputting unit 15, starts an operation of the first measuring mode. First, a display that prompts input of the thickness and the refractive index n of the sample 100 to a measurer is displayed on the displaying unit 14 and when they are input from the inputting unit 15 (step S1), the procedure goes to step S2. The thickness D of the sample 100 is measured in advance.

In the step S2, the control/calculation unit 7 controls a stage 13 to allow the condensing lens 11 to be positioned at a standard position. The standard position is a position where a front focal point of the condensing lens 11 coincides with a rear focal point of the condensing lens 10 and where focusing of the terahertz pulse light to the terahertz light detector is optimized when no sample 100 is arranged. The standard position is stored in the memory of the control/calculation unit 7 in advance.

Then, the control/calculation unit 7 performs reference measurement in a state where no sample 100 is arranged (step S3). That is, the control/calculation unit 7, in a state where no sample 100 is arranged, gives a control signal to the stage 8 as mentioned above to gradually alter the delay time τ and store the detected signal data from the terahertz light detector 6 into the internal memory. As a result, the time-series waveform of the electric field intensity of the terahertz pulse light L5 is obtained.

Then, the control/calculation unit 7 calculates the offset amount δL represented by the equation 7 as the moving amount of the condensing lens 11 according to the equation 7 (step S4). On this occasion, the thickness D and the refractive index n input in the step S1 are used.

Figure 1:
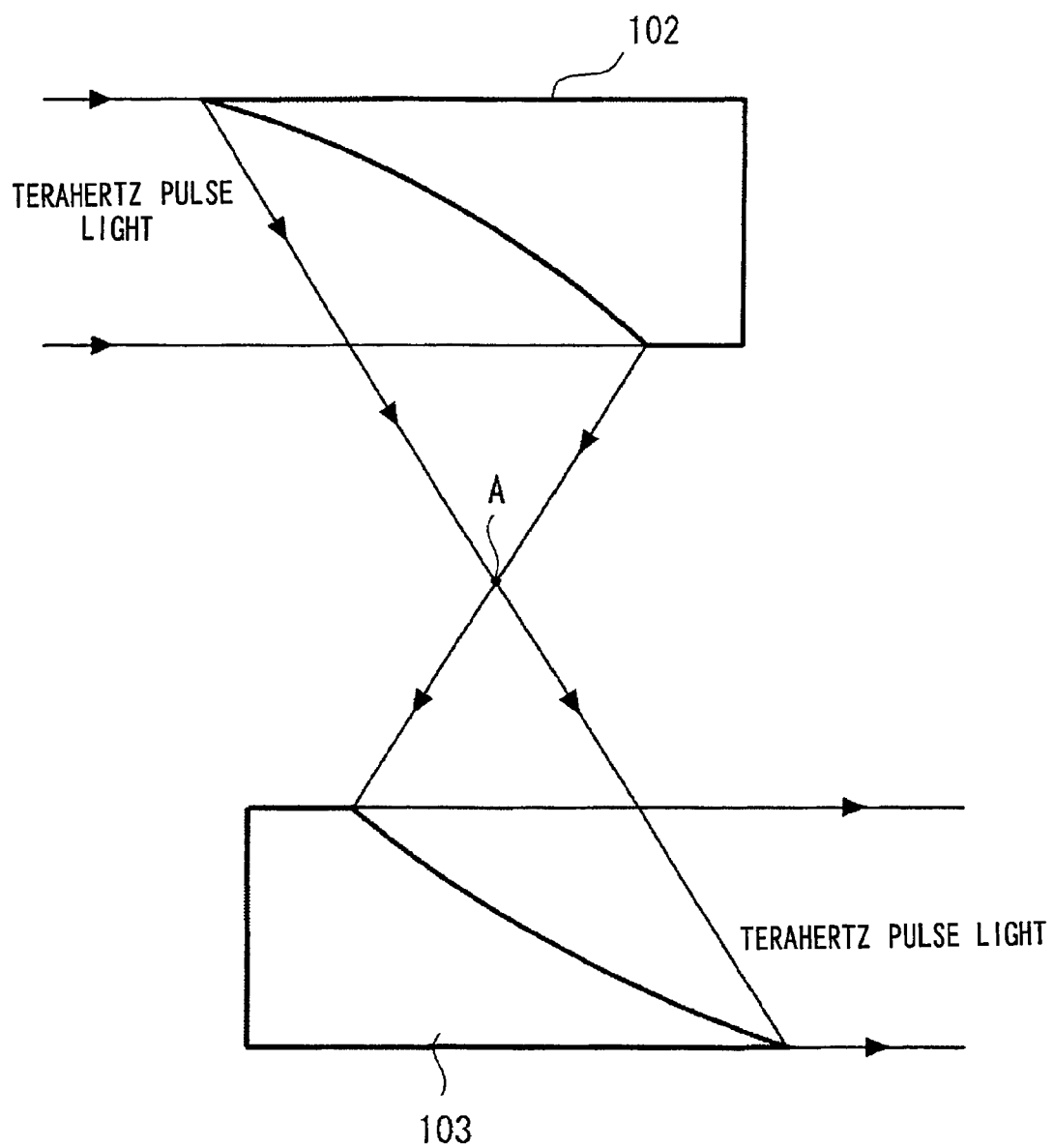
FIG. 1 is a schematic diagram illustrating the state of terahertz pulse light in the vicinity of the second and the third parabolic mirrors in a conventional measuring equipment when no sample is arranged.

Thereafter, the control/calculation unit 7 controls the stage 13 so that the condensing lens 11 is moved from the standard position by the moving amount (offset amount δL) obtained in the step S4 away from where the sample 100 is arranged, and at that position the condensing lens 11 is stopped (step S5). As will be understood from the description related to FIGS. 1 to 3, when the condensing lens 11 is positioned at this position, the focal point of the condensing lens 11 coincides with apparent diverging point of the terahertz pulse light L5 in the state where the sample 100 is arranged at the position shown in FIG. 4. As a result, in the state where the sample 100 is arranged at the position shown in FIG. 4, the terahertz pulse light L5 is converted into a parallel beam by the condensing lens 11 and enters into a parabolic mirror 12. The position of the condensing lens 11 can be said to be a position at which the front focal point of the condensing lens 11 coincides with the rear focal point of the condensing lens 10 in a state where the sample 100 is arranged.

Therefore, after the adjustment of the position of the condensing lens 11 in the step S5, the condensation state of the terahertz pulse light L5 to the terahertz light detector 6 when the sample 100 is arranged at the position shown in FIG. 4 is similar to the condensation state of the terahertz pulse light L5 to the terahertz light detector 6 when the condensing lens 11 is positioned at the above-mentioned standard position and no sample 100 is arranged. This enables optimized focused state to be maintained. Needless to say, this state is better than the focused state of the terahertz pulse light L5 to the terahertz light detector 6 when the condensing lens 11 is positioned at the above-mentioned standard position and the sample 100 is arranged at the position shown in FIG. 4.

Subsequently, the control/calculation unit 7 performs measurement of the sample in a state where the sample 100 is positioned at the position shown in FIG. 4 (step S6). That is, the control/calculation unit 7, in a state where the sample 100 is positioned at the position shown in FIG. 4, gives a control signal to the stage 8 as mentioned above to gradually alter the delay time τ and store the data of detected signal from the terahertz light detector 6, thereby obtaining time-series waveform of the electric field intensity of the terahertz pulse light L5.

Then, the control/calculation unit 7 subjects the time-series waveform for reference obtained in the step S3 and the time-series waveform obtained in the step S6 to Fourier transformation. For each of the waveform components obtained by the Fourier transformation, the component of the time-series waveform obtained in the step S6 is divided by the component of the time-series waveform obtained in the step S3 to prepare spectroscopic data (step S7). Thereafter, the control/calculation unit 7 allows the spectroscopic data on the displaying unit 14 and terminates the first measuring mode.

In the first measuring mode, either in the reference measurement in the step S3 or in the sample measurement in the step S6, the condensation state of the terahertz pulse light L5 to the terahertz light detector 6 is in a similarly optimized focused state. Therefore, measurement errors due to the thickness D and the refractive index n of the sample 100 can be decreased.

Figure 6:
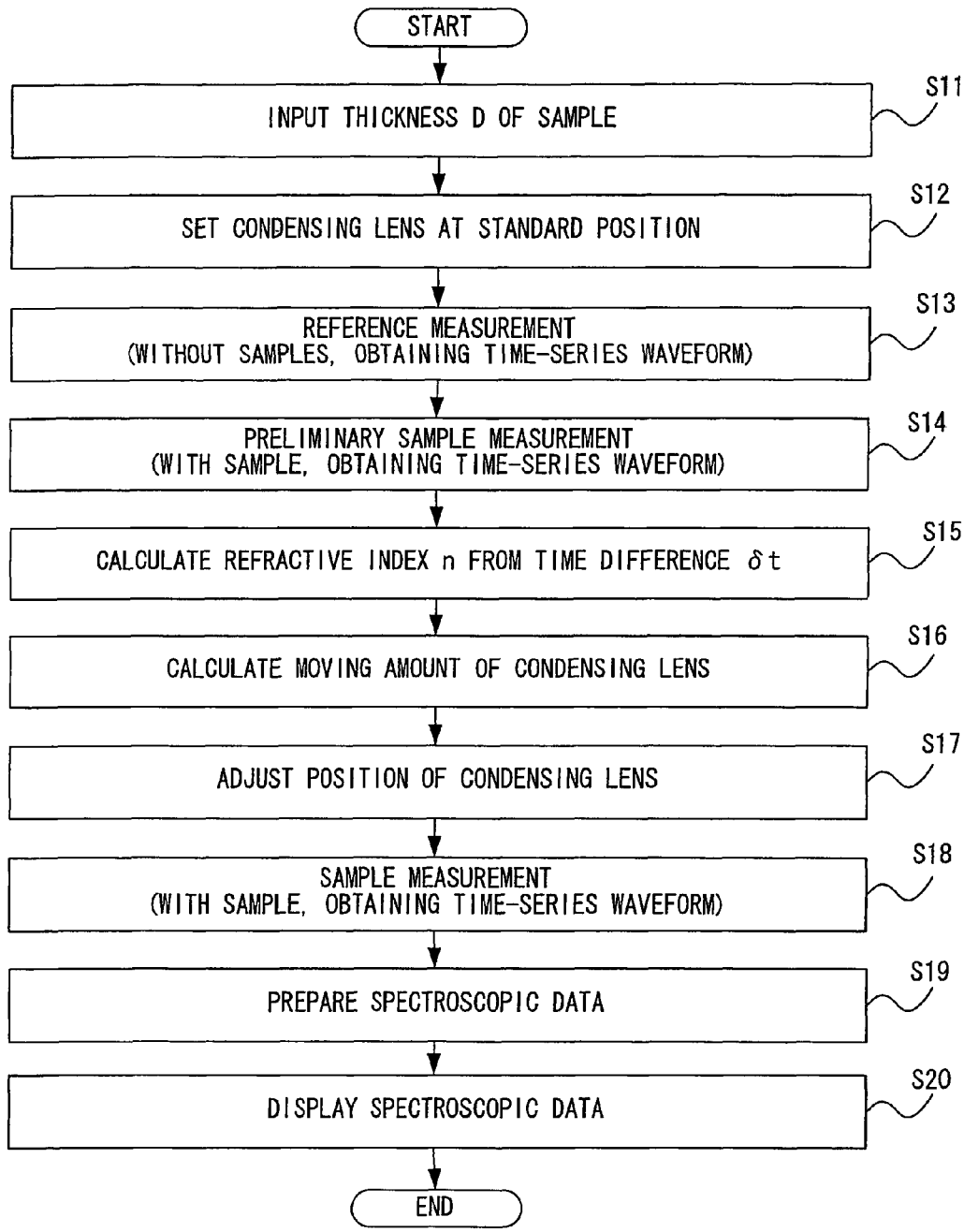
FIG. 6 is a schematic flowchart illustrating an operation in a second measuring mode of the measuring equipment according to the first embodiment of the present invention.

The second measuring mode is a measuring mode in which reference measurement is performed in a state where no sample 100 is arranged and the spectroscopic data of the sample 100 is obtained when the refractive index n of the sample 100 is unknown. FIG. 6 is a schematic flowchart illustrating operation of the second measuring mode.

The control/calculation unit 7, when given instruction for the second measuring mode by the inputting unit 15, starts an operation of the second measuring mode. First, a display that prompts input of the thickness D of the sample 100 to a measurer is displayed on the displaying unit 14 and when it is input through the inputting unit 15 (step S11), the control/calculation unit 7 controls the stage 13 to allow the condensing lens 11 to be positioned at the standard position (step S12).

Then, the control/calculation unit 7 performs reference measurement in a state where no sample 100 is arranged in the same manner as in the step S3 to obtain time-series waveform of the electric field intensity of the terahertz pulse light L5 (step S13).

Then, the control/calculation unit 7 performs preliminary sample measurement similarly to the sample measurement in the step S6 in a state where the condensing lens 11 remains to be positioned at the standard position (step S14). That is, the control/calculation unit 7 obtains time-series waveform of the electric field intensity of the terahertz pulse light in a state where the condensing lens 11 is positioned at the standard position and where the sample 100 is positioned at the position shown in FIG. 4.

Figure 11:
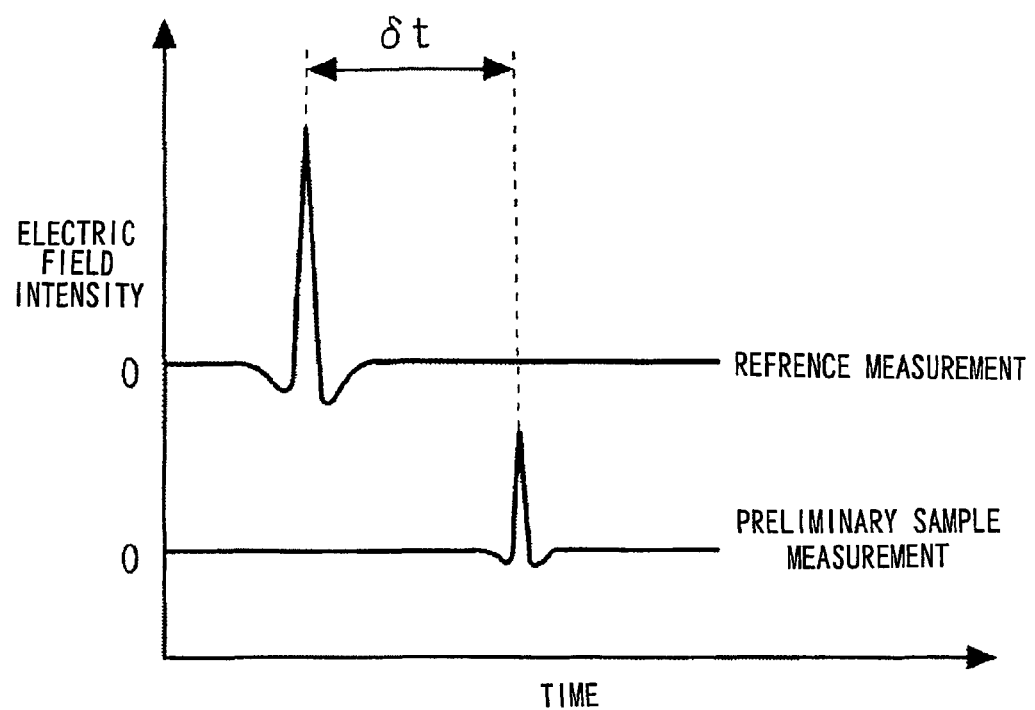
FIG. 11 is a diagram illustrating examples of time-series waveform obtained by reference measurement and of time-series waveform obtained by preliminary measurement of a sample.

FIG. 11 is a diagram illustrating examples of a time-series waveform obtained by the reference measurement in the step S13 and a time-series waveform obtained by the preliminary sample measurement in the step S14. As already described, assuming that the thickness of the sample 100 is D and the refractive index of the sample 100 is n, and further that a time difference between peaks of the both time-series waveforms is δt as shown in FIG. 11 and velocity of light is c, then the following equation 8 is obtained.

$$n=(\delta t/D)\cdot c+1 \quad \text{(Equation 8)}$$

After the step S14, the control/calculation unit 7 obtains the time difference δt between the peaks of the both time-series waveforms obtained in the steps S13 and S14, respectively and utilizing the time difference δt, calculates the refractive index n of the sample 100 according to the equation 8 (step S15). On this occasion, the thickness D of the sample 100 input in the step S11 is used.

Then, the control/calculation unit 7 calculates the offset amount δL represented by the equation 7 according to the equation 7 (step S16). On this occasion, the thickness D of the sample 100 input in the step S11 and the refractive index n of the sample 100 calculated in the step S15 are used.

Thereafter, the control/calculation unit 7 controls the stage 13 so that the condensing lens 11 is moved from the standard position by the moving amount (offset amount δL) obtained in the step S16 away from where the sample 100 is arranged, and at that position the condensing lens 11 is stopped (step S17). When the condensing lens 11 is positioned at this position, similarly to the case of the above-mentioned step S5, the condensation state of the terahertz pulse light L5 to the terahertz light detector 6 when the sample 100 is arranged at the position shown in FIG. 4 is similar to the condensation state of the terahertz pulse light L5 to the terahertz light detector 6 when the condensing lens 11 is positioned at the above-mentioned standard position and no sample 100 is arranged so that optimized focused state can be maintained.

Subsequently, the control/calculation unit 7 performs the processes in steps S18 to S20 similar to those in the steps S6 to S8 and terminates the second measuring mode. Preparation of the spectroscopic data in the step S19 is performed using the reference time-series waveform obtained by the reference measurement in the step S13 and the time-series waveform obtained in the sample measurement in the step S18 but not the time-series waveform obtained by the preliminary sample measurement in the step S14.

In the second measuring mode, like in the first measuring mode, either in the reference measurement in the step S13 or in the sample measurement in the step S18, the condensation state of the terahertz pulse light L5 to the terahertz light detector 6 is in a similarly optimized focused state. Therefore, measurement errors due to the thickness D and the refractive index n of the sample 100 can be decreased.

Figure 7:
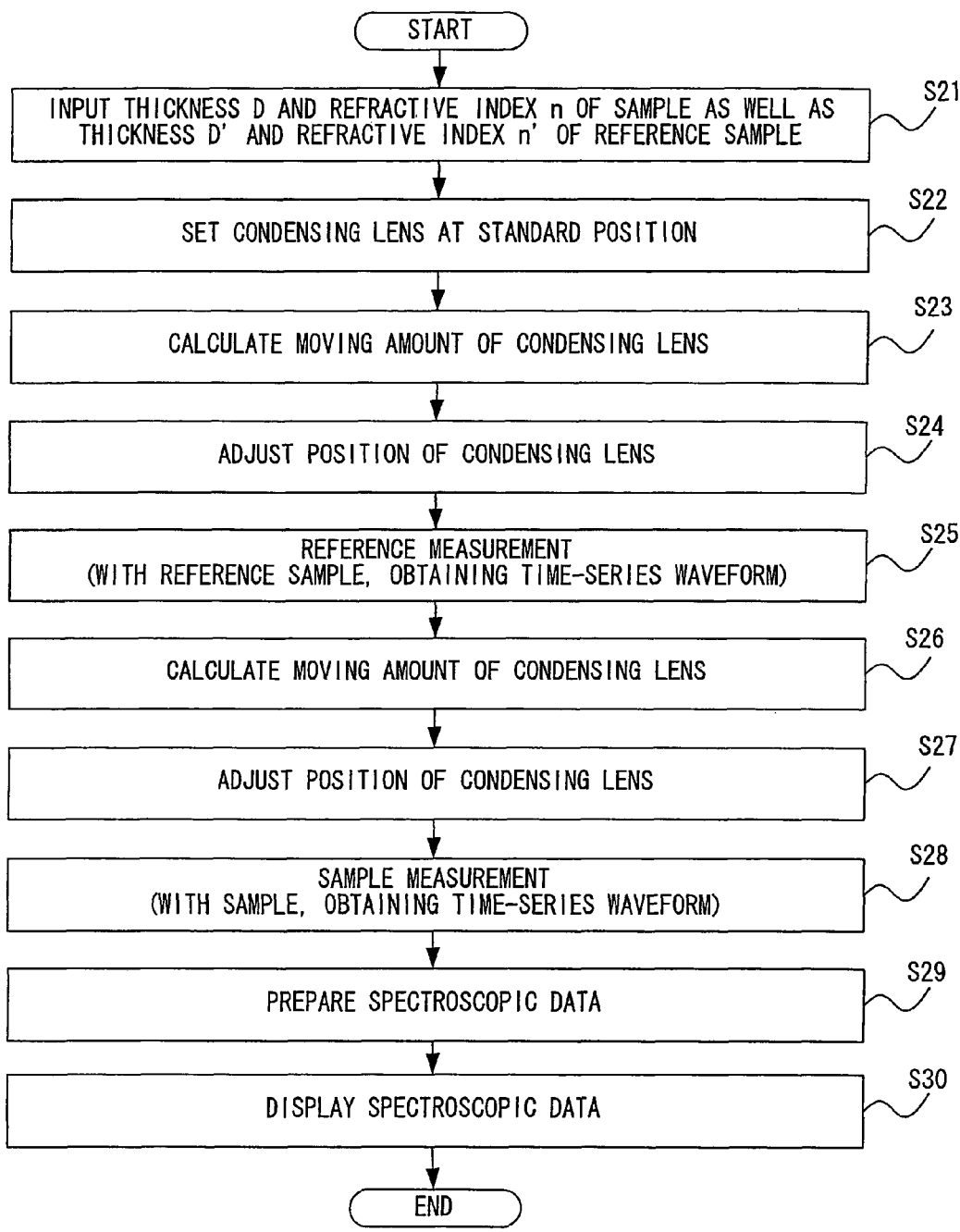
FIG. 7 is a schematic flowchart illustrating an operation in a third measuring mode of the measuring equipment according to the first embodiment of the present invention.

The third measuring mode is a measuring mode in which reference measurement is performed in a state where a reference sample is arranged and the spectroscopic data of the sample 100 is obtained when the refractive index n of the sample 100 and the refractive index n' of the reference sample are known. FIG. 7 is a schematic flowchart illustrating operation of the third measuring mode.

The control/calculation unit 7, when given instruction for the third measuring mode by the inputting unit 15, starts an operation of the third measuring mode. First, a display that prompts input of the thickness D and the refractive index n of the sample 100 as well as the thickness D' and the refractive index n' of the reference sample to a measurer is displayed on the displaying unit 14 and when they are input through the inputting unit 15 (step S21), the control/calculation unit 7 controls the stage 13 to allow the condensing lens 11 to be positioned at the standard position (step S22).

Then, the control/calculation unit 7 calculates an offset amount δL' represented by the equation 9 relative to the reference sample as the moving amount of the condensing lens 11 according to the equation 9 (step S23). On this occasion, the thickness D' and the refractive index n' of the reference sample input in the step S21 are used. The equation 9 is obtained by rewriting the equation 7 so as to conform to the reference sample.

$$\delta L'=D'(1-1/n') \quad \text{(Equation 9)}$$

Thereafter, the control/calculation unit 7 controls the stage 13 so that the condensing lens 11 is moved from the standard position by the moving amount (offset amount δL') obtained in the step S23 away from where the sample 100 is arranged, and at that position the condensing lens 11 is stopped (step S24).

Subsequently, the control/calculation unit 7 performs reference measurement in a state where the reference sample instead of the sample 100 is positioned at the position of the sample 100 shown in FIG. 4 to obtain time-series waveform of the electric field intensity of the terahertz pulse light L5 (step S25).

Then, the control/calculation unit 7 calculates the value ΔL represented by the equation 10 below as the moving amount of the condensing lens 11 (step S26). On this occasion, the thickness D and the refractive index n of the sample 100 as well as the thickness D' and the refractive index n' of the reference sample input in the step S21 are used. The moving amount ΔL is used taking into consideration the fact that currently the condensing lens 11 is positioned at a position remote from the standard position by an offset amount δL' and the moving amount ΔL is an amount from the current position necessary for positioning the condensing lens 11 at a position away from the standard position by the offset amount δL relative to the sample 100.

$$\Delta L=\delta L-\delta L'=D\cdot(1-1/n)-D'\cdot(1-1/n') \quad \text{(Equation 10)}$$

Then, the control/calculation unit 7 controls the stage 13 so that the condensing lens 11 is moved from the current position by the moving amount ΔL obtained in the step S26, and at that position the condensing lens 11 is stopped (step S27). When ΔL is positive, the condensing lens 11 is moved in the direction away from the position where the sample 100 is arranged while when ΔL is negative, the condensing lens 11 is moved in the opposite direction.

Thereafter, the control/calculation unit 7 performs the processes in steps S28 to S30 similar to those in the steps S6 to S8 and terminates the third measuring mode. Preparation of the spectroscopic data in the step S29 is performed using the reference time-series waveform obtained by the reference measurement in the step S25 and the time-series waveform obtained in the sample measurement in the step S28.

In the third measuring mode, while a reference sample is used in the reference measurement, either in the reference measurement in the step S25 or in the sample measurement in the step S28, the condensation state of the terahertz pulse light L5 to the terahertz light detector 6 is in a similarly optimized focused state. Therefore, measurement errors due to the thickness D and the refractive index n of the sample 100 as well as the thickness D' and the refractive index n' of the reference sample can be decreased.

Figure 8:
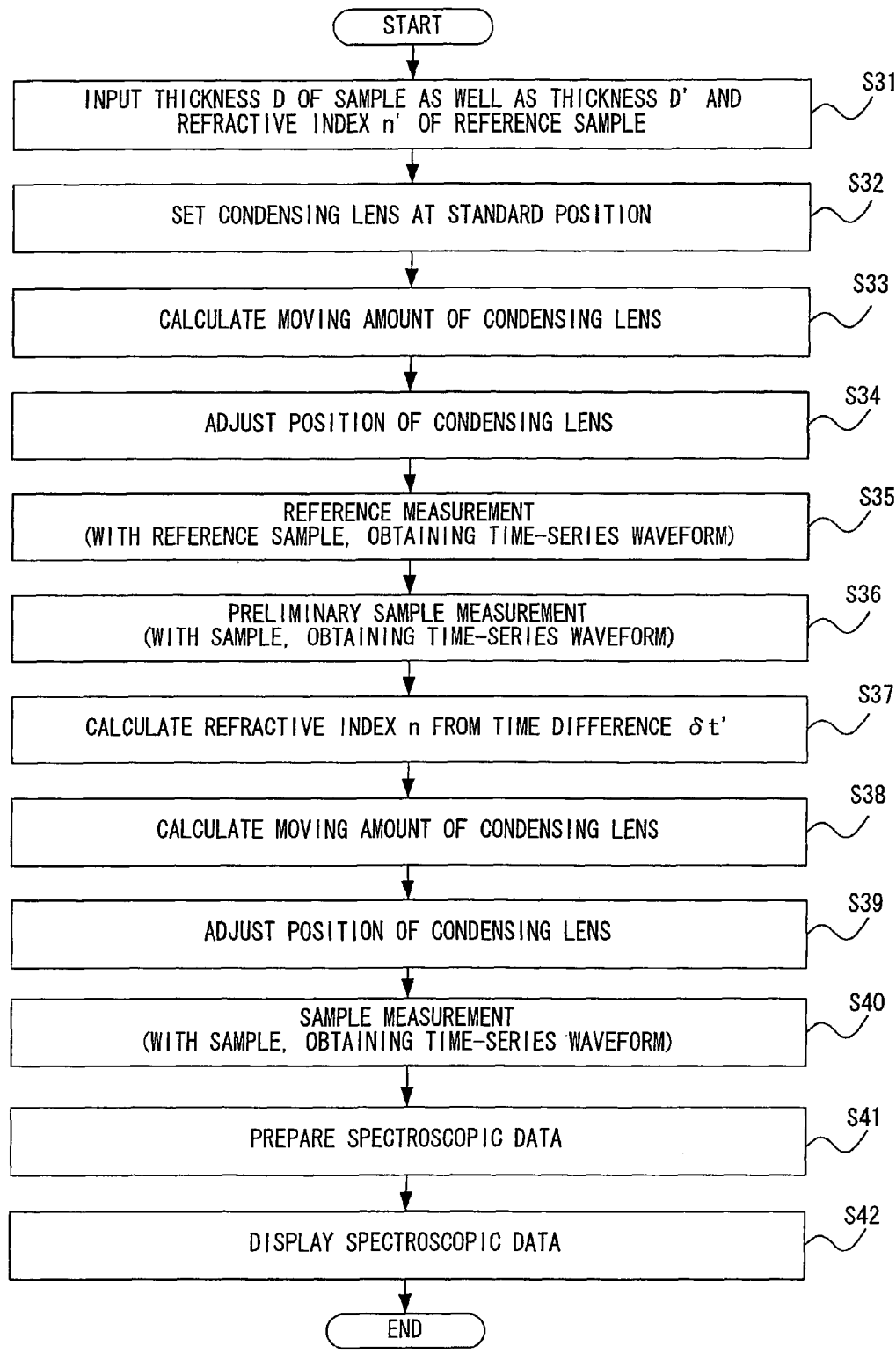
FIG. 8 is a schematic flowchart illustrating an operation in a fourth measuring mode of the measuring equipment according to the first embodiment of the present invention.

The fourth measuring mode is a measuring mode in which reference measurement is performed in a state where a reference sample is arranged and the spectroscopic data of the sample 100 is obtained when the refractive index n of the sample 100 is unknown and the refractive index n' of the reference sample is known. FIG. 8 is a schematic flowchart illustrating an operation of the fourth measuring mode.

The control/calculation unit 7, when given instruction for the fourth measuring mode by the inputting unit 15, starts an operation of the fourth measuring mode. First, a display that prompts input of the thickness D and the refractive index n of the sample 100 as well as the thickness D' and the refractive index n' of the reference sample to a measurer is displayed on the displaying unit 14 and when they are input through the inputting unit 15 (step S31), the control/calculation unit 7 controls the stage 13 to allow the condensing lens 11 to be positioned at the standard position (step S32).

Then, the control/calculation unit 7 calculates the offset amount δL' represented by the equation 9 relative to the reference sample as the moving amount of the condensing lens 11 according to the equation 9 (step S33). On this occasion, the thickness D' and the refractive index n' of the reference sample input in the step S31 are used.

Thereafter, the control/calculation unit 7 controls the stage 13 so that the condensing lens 11 is moved from the standard position by the moving amount (offset amount δL') obtained in the step S33 away from where the reference sample or the sample 100 is arranged, and at that position the condensing lens 11 is stopped (step S34).

Subsequently, the control/calculation unit 7 performs reference measurement in a state where the reference sample instead of the sample 100 is positioned at the position of the sample 100 shown in FIG. 4 to obtain a time-series waveform of the electric field intensity of the terahertz pulse light L5 (step S35).

Then, the control/calculation unit 7 performs preliminary sample measurement similarly to the sample measurement in the step S6 in a state where the condensing lens 11 remains to be positioned at the position adjusted in the step S34 (step S36). That is, the control/calculation unit 7 obtains a time-series waveform of the electric field intensity of the terahertz pulse light in a state where the condensing lens 11 is positioned at that position and where the sample 100 is positioned at the position shown in FIG. 4.

Then, the control/calculation unit 7 calculates a time difference δt' between a peak of the time-series waveform obtained in the step S35 and a peak of the time-series waveform obtained in the step S36 and using this time difference δt', the control/calculation unit 7 calculates the refractive index n of the sample 100 according to the equation 11 below (step S37). On this occasion, the thickness of the sample 100 as well as the thickness D' and the refractive index n' of the reference sample input in the step S31 and the refractive index n of the sample 100 calculated in the step S37 are used. In the equation 11, c represents velocity of light.

$$n=((\delta t' \cdot c+(n'-1)\cdot D')/D)+1 \quad \text{(Equation 11)}$$

Subsequently, the control/calculation unit 7 calculates the amount ΔL represented by the equation 10 as the moving amount of the condensing lens 11 (step S38). On this occasion, the thickness D of the sample 100, the thickness D' and the refractive index n' of the reference sample input in the step S31 and the refractive index n of the sample 100 calculated in the step S37 are used.

Then, the control/calculation unit 7 controls the stage 13 so that the condensing lens 11 is moved from the current position by the moving amount ΔL obtained in the step S38, and at that position the condensing lens 11 is stopped (step S39). When ΔL is positive, the condensing lens 11 is moved in the direction away from the position where the sample 100 is arranged while when ΔL is negative, the condensing lens 11 is moved in the opposite direction.

Thereafter, the control/calculation unit 7 performs the processes in steps S40 to S42 similar to those in the steps S6 to S8 and terminates the fourth measuring mode. Preparation of the spectroscopic data in the step S41 is performed using the reference time-series waveform obtained by the reference measurement in the step S35 and the time-series waveform obtained in the sample measurement in the step S40 but not the time-series waveform obtained by the preliminary sample measurement in the step S36.

In the fourth measuring mode, while a reference sample is used in the reference measurement, like the third measuring mode, either in the reference measurement in the step S25 or in the sample measurement in the step S28, the condensation state of the terahertz pulse light L5 to the terahertz light detector 6 is in a similarly optimized focused state. Therefore, measurement errors due to the thickness D and the refractive index n of the sample 100 as well as the thickness D' and the refractive index n' of the reference sample can be decreased.

Figure 9:
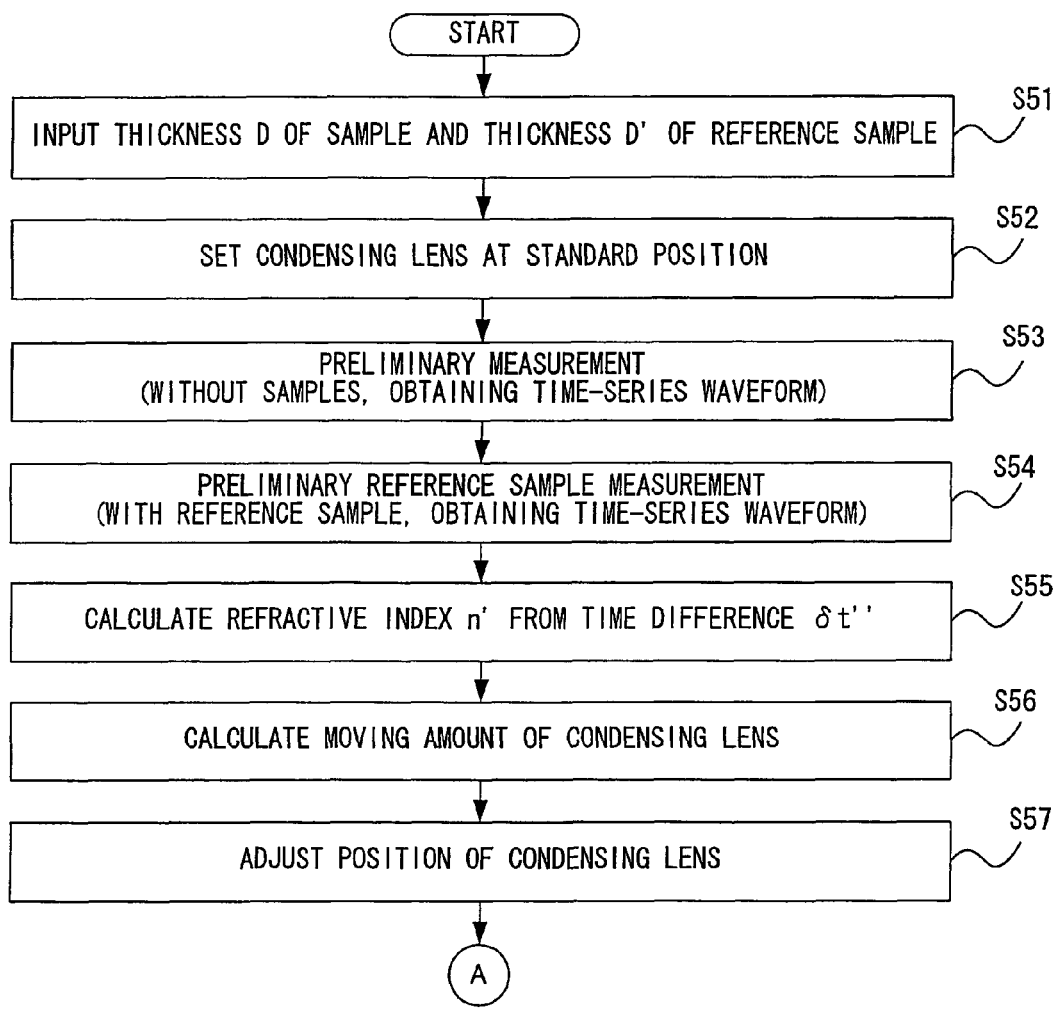
FIG. 9 is a schematic flowchart illustrating an operation in a fifth measuring mode of the measuring equipment according to the first embodiment of the present invention.
Figure 10:
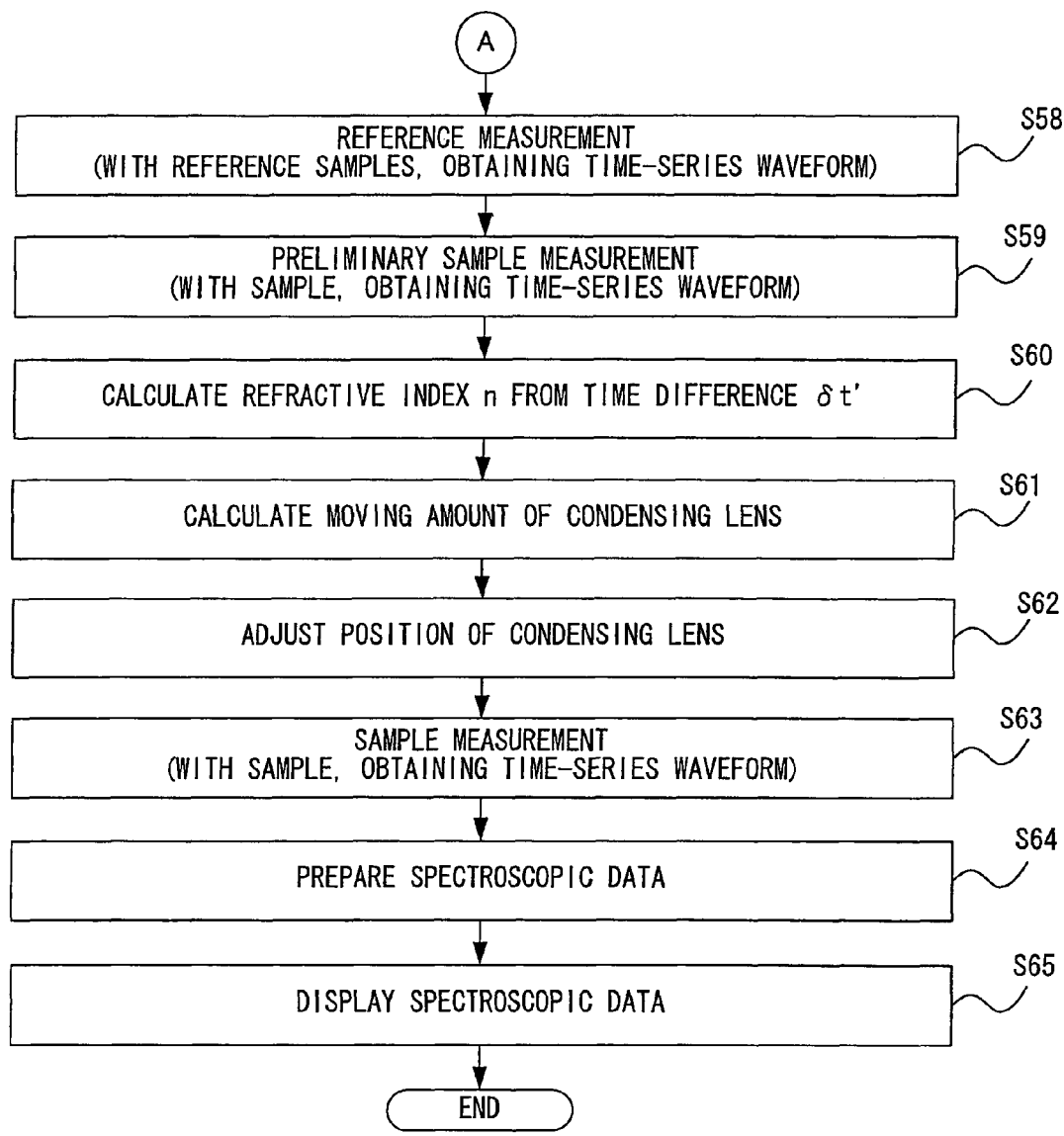
FIG. 10 is a schematic flowchart continued from FIG. 9.

The fifth measuring mode is a measuring mode in which reference measurement is performed in a state where a reference sample is arranged and the spectroscopic data of the sample 100 is obtained when the refractive index n of the sample 100 and the refractive index n' of the reference sample are unknown. FIGS. 9 and 10 are each a schematic flowchart illustrating an operation of the fifth measuring mode.

The control/calculation unit 7, when given instruction for the fifth measuring mode by the inputting unit 15, starts an operation of the fifth measuring mode. First, a display that prompts input of the thickness D of the sample 100 and the thickness D' of the reference sample to a measurer is displayed on the displaying unit 14 and when they are input through the inputting unit 15 (step S51), the control/calculation unit 7 controls the stage 13 to allow the condensing lens 11 to be positioned at the standard position (step S52).

Then, the control/calculation unit 7 performs preliminary measurement similar to that in the step S3 (step S53). That is, the control/calculation unit 7 obtains a time-series waveform of the electric field intensity of the terahertz pulse light L5 in a state where no sample 100 is arranged.

Then, the control/calculation unit 7 performs preliminary sample measurement for reference similar to the reference measurement in the step S25 in a state where the condensing lens 11 remains to be positioned at the standard position (step S54). That is, the control/calculation unit 7 obtains a time-series waveform of the electric field intensity of the terahertz pulse light L5 in a state where the condensing lens 11 is positioned at the standard position and where the reference sample instead of the sample 100 is positioned at the position of the sample 100 shown in FIG. 4.

Then, the control/calculation unit 7 calculates a time difference δt" between a peak of the time-series waveform obtained in the step S53 and a peak of the time-series waveform obtained in the step S54 and using this time difference δt", the control/calculation unit 7 calculates the refractive index n' of the reference sample according to the equation 12 below (step S55). On this occasion, the thickness D' of the reference sample input in the step S51 is used. In the equation 12, c represents velocity of light.

$$n'=((\delta t''/D')\cdot c)+1 \quad \text{(Equation 12)}$$

Then, the control/calculation unit 7 calculates an offset amount δL' represented by the equation 9 relative to the reference sample as the moving amount of the condensing lens 11 according to the equation 9 (step S56). On this occasion, the thickness D' of the reference sample input in the step S51 and the refractive index n' of the reference sample input in the step S55 are used.

Thereafter, the control/calculation unit 7 controls the stage 13 so that the condensing lens 11 is moved from the standard position by the moving amount (offset amount δL') obtained in the step S56 away from where the sample 100 is arranged, and at that position the condensing lens 11 is stopped (step S57).

Subsequently, the control/calculation unit 7 performs reference measurement in a state where the reference sample instead of the sample 100 is positioned at the position of the sample 100 shown in FIG. 4 to obtain a time-series waveform of the electric field intensity of the terahertz pulse light L5 (step S58).

Then, the control/calculation unit 7 performs preliminary sample measurement similar to the sample measurement in the step S6 in a state where the condensing lens 11 remains to be positioned at the position adjusted in the step S57 (step S59). That is, the control/calculation unit 7 obtains a time-series waveform of the electric field intensity of the terahertz pulse light L5 in a state where the condensing lens 11 is positioned at that position and the sample 100 is positioned at the position shown in FIG. 4.

Then, the control/calculation unit 7 calculates a time difference δt' between a peak of the time-series waveform obtained in the step S58 and a peak of the time-series waveform obtained in the step S59 and using this time difference δt', the control/calculation unit 7 calculates the refractive index n of the sample 100 according to the equation 11 (step S60). On this occasion, the thickness D of the sample 100 and the thickness D' of the reference sample input in the step S31 as well as the refractive index n' of the reference sample calculated in the step S55 are used.

Subsequently, the control/calculation unit 7 calculates the value ΔL represented by the equation 10 as the moving amount of the condensing lens 11 (step S61). On this occasion, the thickness D of the sample 100 and the thickness D' of the reference sample input in the step S51 and the refractive index n of the sample 100 calculated in the step S60 and the refractive index n' of the reference sample calculated in the step S55 are used.

Then, the control/calculation unit 7 controls the stage 13 so that the condensing lens 11 is moved from the current position by the moving amount ΔL obtained in the step S61, and at that position the condensing lens 11 is stopped (step S62). When ΔL is positive, the condensing lens 11 is moved in the direction away from the position where the sample 100 is arranged while when ΔL is negative, the condensing lens 11 is moved in the opposite direction.

Thereafter, the control/calculation unit 7 performs the processes in steps S63 to S65 similar to those in the steps S6 to S8 and terminates the fifth measuring mode. Preparation of the spectroscopic data in the step S64 is performed using the reference time-series waveform obtained by the reference measurement in the step S58 and the time-series waveform obtained in the sample measurement in the step S63.

In the fifth measuring mode, while a reference sample is used in the reference measurement, like the third measuring mode, either in the reference measurement in the step S25 or in the sample measurement in the step S28, the condensation state of the terahertz pulse light L5 to the terahertz light detector 6 is in a similarly optimized focused state. Therefore, measurement errors due to the thickness D and the refractive index n of the sample 100 as well as the thickness D' and the refractive index n' of the reference sample can be decreased.

As described above, according to the present embodiment, the measurement errors due to the thickness D and the refractive index n of the sample 100 can be decreased.

In the present embodiment, as described above, a decrease in condensation state of the terahertz pulse light L5 to the terahertz light detector 6 (so-called blurring) due to the thickness D and the refractive index n of the sample 100 is prevented by adjusting the position of the condensing lens 11 on the optical axis, thereby decreasing measurement errors due to the thickness D and the refractive index n of the sample 100.

Since the transmissive optical device is adjusted for its position for decreasing measurement errors, when the position adjustment is performed, the light path length from the terahertz light generator 3 to the terahertz light detector 6 does not change at all and reference measurement can be performed at the same light path length, thus giving no influence on the obtained time-series waveform of the terahertz pulse light by the pump-probe method. Therefore, when the position of the movable mirror 4 is being altered upon obtaining a time-series waveform of terahertz pulse light by the pump-probe method, reference measurement and sample measurement can be performed in quite the same manner, so that an advantageous effect can be obtained in that it is not necessary to consider an offset amount associated with position adjustment of the moving mirror to decrease measurement errors.

Further, according to the present embodiment, also an advantage can be obtained in that since only the condensing lens 11 is to be adjusted for its position for decreasing measurement errors, the position adjusting mechanism (the stage 13 in the present embodiment) is small and inexpensive as compared with the case where many optical devices are adjusted for their position as a block.

Second Embodiment

Figure 12:
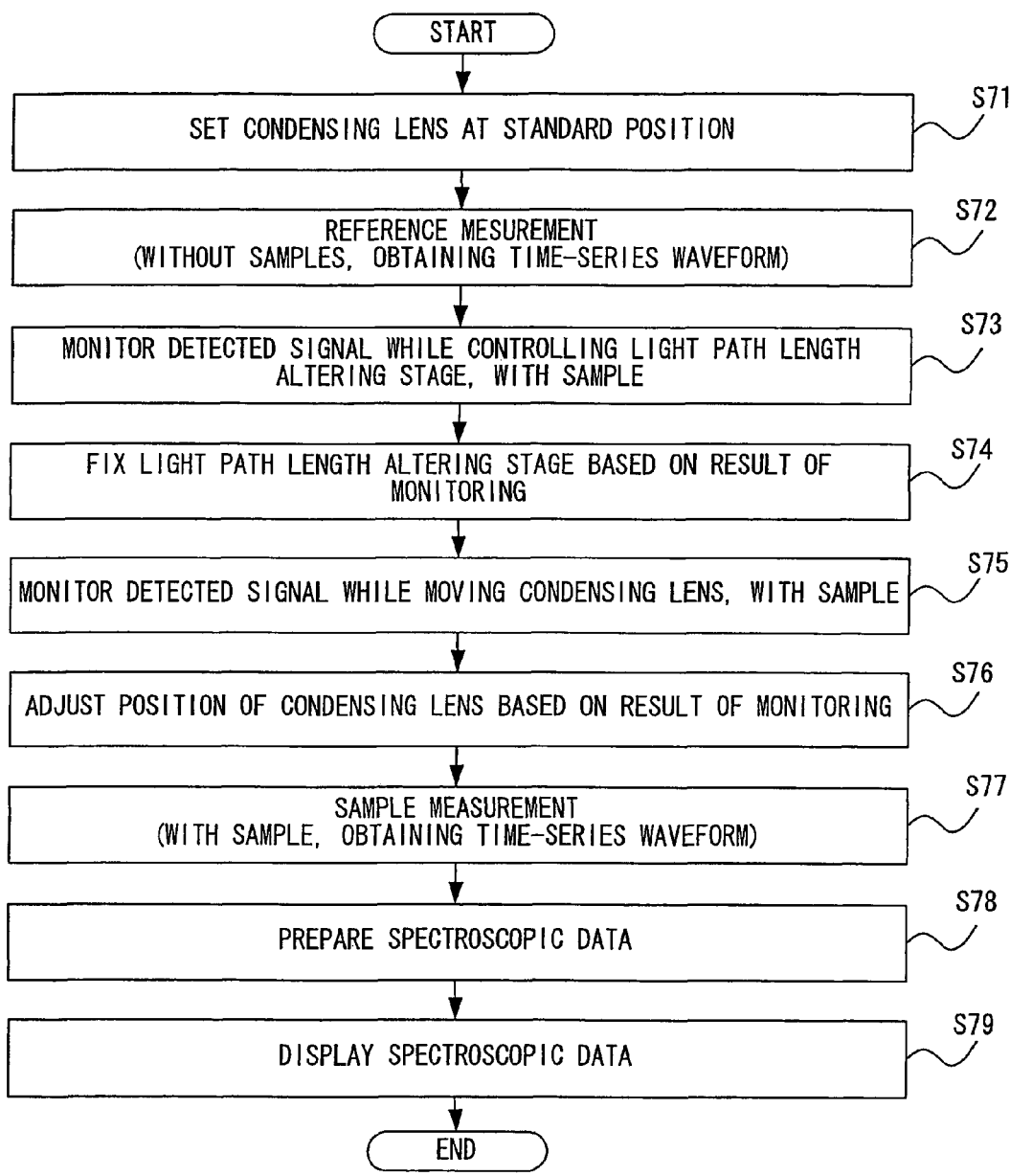
FIG. 12 is a schematic flowchart illustrating an operation in a sixth measuring mode of measuring equipment according to a second embodiment of the present invention.
Figure 13:
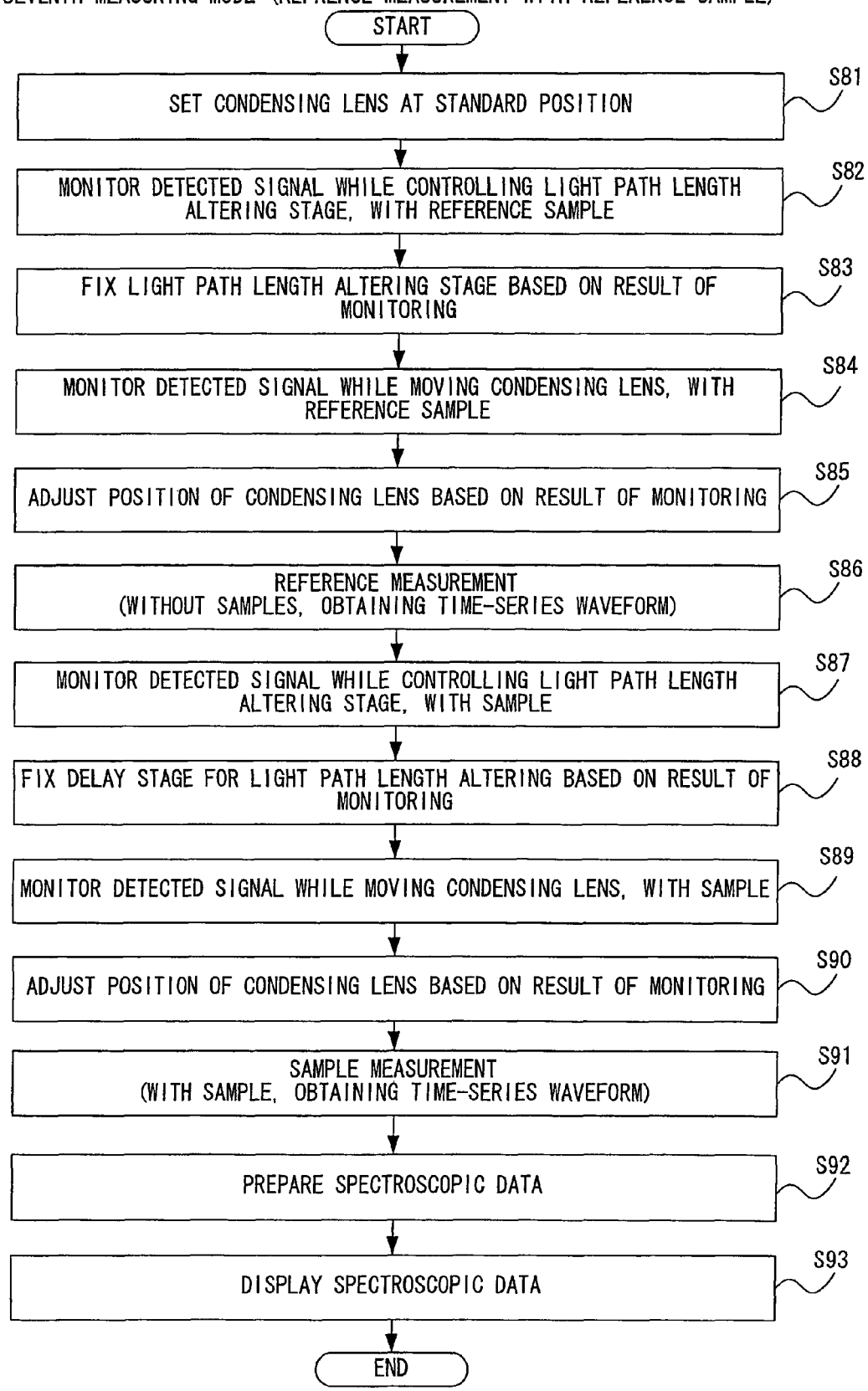
FIG. 13 is a schematic flowchart illustrating an operation in a seventh measuring mode of the measuring equipment according to the second embodiment of the present invention.

FIGS. 12 and 13 are flowcharts illustrating operations of sixth and seventh measuring modes, respectively, of the measuring equipment according to the second embodiment of the present invention.

Only the difference between the present embodiment and the first embodiment is in that in the first embodiment, the control/calculation unit 7 is configured to perform the first to fifth measuring modes shown in FIGS. 5 to 9, respectively, while in the present embodiment the control/calculation unit 7 is configured to perform sixth and seventh measuring modes shown in FIGS. 12 and 13, respectively. However, in the present invention, the control/calculation unit 7 may be configured to perform either one of the sixth or the seventh measuring mode only.

In the first embodiment, as described above, the moving amount of the condensing lens 11 is obtained in advance by calculation to perform adjustment of the position of the condensing lens 11. In contrast, in the present embodiment, no such calculation is performed and the adjustment of the position of the condensing lens 11 is performed utilizing the fact that the more focused the terahertz pulse light L5 to the terahertz light detector 6, the greater the detected signal of the terahertz light detector 6.

The sixth measuring mode is a measuring mode in which reference measurement is performed in a state where no sample 100 is arranged to obtain spectroscopic data of the sample 100.

The control/calculation unit 7, when given instruction for the sixth measuring mode by the inputting unit 15, starts an operation of the sixth measuring mode. As shown in FIG. 12, first, processes in steps S71 and S72 that are the same as the steps S2 and S3, respectively, are performed.

Then, the control/calculation unit 7 monitors detected signals from the terahertz light detector 6 while gradually altering the delay time τ by giving a control signal to the light path length altering stage 8 in a state where the sample 100 is positioned at the position shown in FIG. 4 (step S73), and based on the result of the monitoring, the control/calculation unit 7 fixes the light path length altering stage 8 to a position where the detected signal from the terahertz light detector 6 becomes maximum (step S74).

Then, the control/calculation unit 7 monitors detected signals from the terahertz light detector 6 while giving a control signal to the stage 13 in a state where the sample 100 is arranged at the position shown in FIG. 4 to alter the position of the condensing lens 11 (step. S75), and based on the result of the monitoring, the control/calculation unit 7 fixes the light path length altering stage 8 to a position where the detected signal from the terahertz light detector 6 becomes maximum (step S76).

Subsequently, the control/calculation unit 7 performs the processes in steps S77 to S79 similar to those in the steps S6 to S8 and terminates the sixth measuring mode. Preparation of the spectroscopic data in the step S78 is performed using the reference time-series waveform obtained by the reference measurement in the step S72 and the time-series waveform obtained in the sample measurement in the step S77.

The more focused the terahertz pulse light L5 to the terahertz light detector 6 becomes, the greater the detected signal from the terahertz light detector 6 becomes. Therefore, the condensation state of the terahertz pulse light to the terahertz light detector 6 in the sixth measuring mode is similarly optimized focused state either in the reference measurement in the step S72 or in the sample measurement in the step S77. Therefore, the measurement errors due to the thickness D and the refractive index n of the sample 100 can be decreased.

The seventh measuring mode is a measuring mode in which reference measurement is performed in a state where a reference sample is arranged to obtain spectroscopic data of the sample 100.

The control/calculation unit 7, when given instruction for the seventh measuring mode by the inputting unit 15, starts an operation of the seventh measuring mode. As shown in FIG. 13, first, the control/calculation unit 7 controls the stage 13 to position the condensing lens 11 at the standard position (step S81).

Then, the control/calculation unit 7 monitors detected signals from the terahertz light detector 6 while gradually altering the delay time τ by giving a control signal to the light path length altering stage 8 in a state where the reference sample instead of the sample 100 is positioned at the position of the sample 100 shown in FIG. 4 (step S82), and based on the result of the monitoring, the control/calculation unit 7 fixes the light path length altering stage 8 to a position where the detected signal from the terahertz light detector 6 becomes maximum (step S83).

Then, the control/calculation unit 7 monitors detected signals from the terahertz light detector 6 while giving a control signal to the stage 13 in a state where the reference sample is arranged as it is to alter the position of the condensing lens 11 (step S84), and based on the result of the monitoring, the control/calculation unit 7 fixes the condensing lens 11 to a position where the detected signal from the terahertz light detector 6 becomes maximum (step S85).

Thereafter, the control/calculation unit 7 performs reference measurement in a state where the reference sample is arranged as it is to obtain a time-series waveform of the electric field intensity of the terahertz pulse light L5 (step S86).

Then, the control/calculation unit 7 performs processes in steps S87 to S93 similar to those in the steps S73 to S79 and terminates the seventh measuring mode. Preparation of the spectroscopic data in the step S92 is performed using the reference time-series waveform obtained by the reference measurement in the step S86 and the time-series waveform obtained in the sample measurement in the step S91.

In the seventh measuring mode, a reference sample is used in the reference measurement. However, since the more focused the terahertz pulse light L5 to the terahertz light detector 6, the greater the detected signal from the terahertz light detector 6, the condensation state of the terahertz pulse light to the terahertz light detector 6 in the sixth measuring mode is in a similarly optimized focused state either in the reference measurement in the step S86 or in the sample measurement in the step S91. Therefore, the measurement errors due to the thickness D and the refractive index n of the sample 100 as well as the thickness D' and the refractive index n' of the reference sample can be decreased.

According to the present embodiment, also a similar advantage to that of the first embodiment can be obtained.

Third Embodiment

Figure 14:
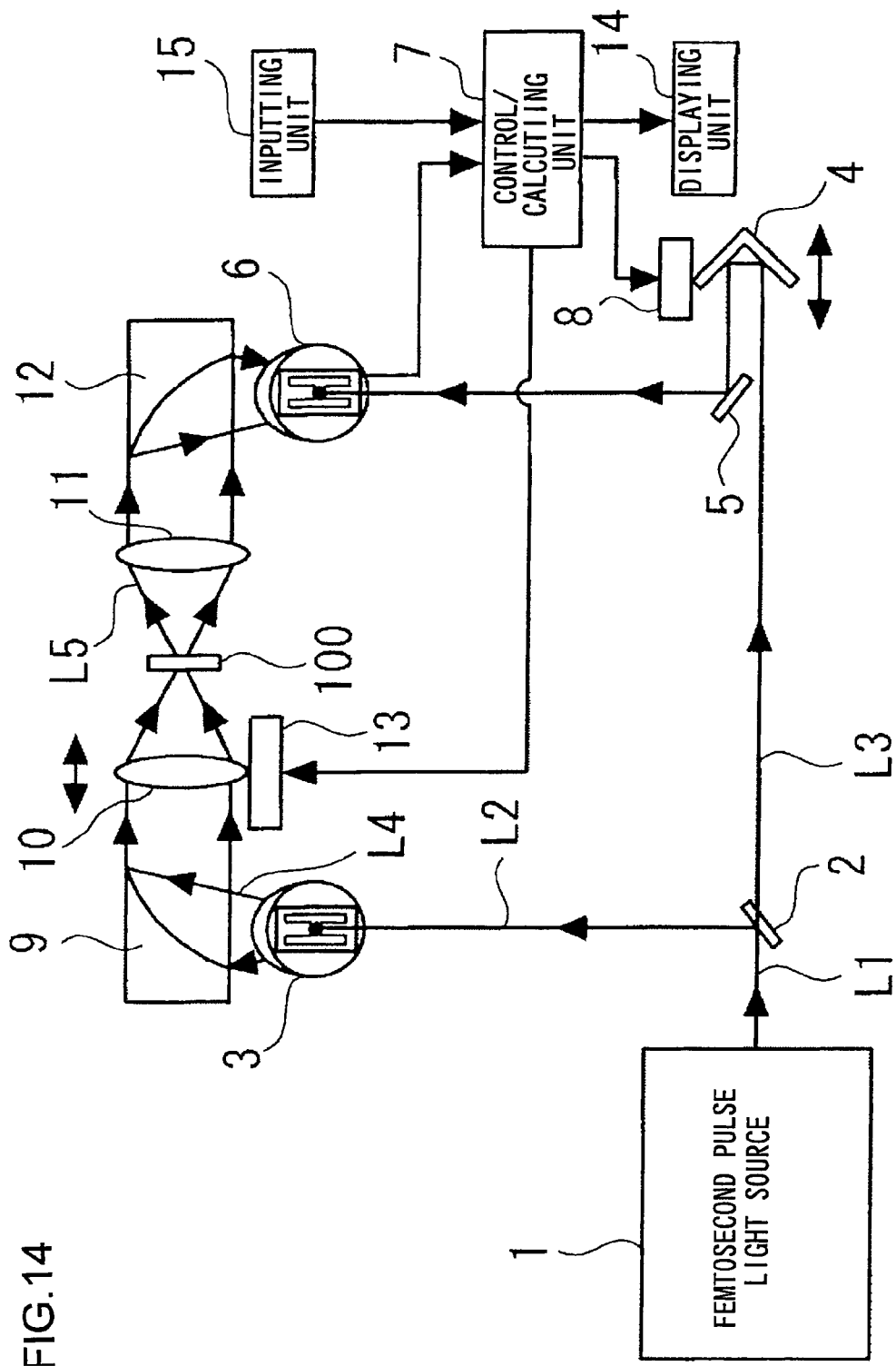
FIG. 14 is a schematic configuration diagram schematically illustrating measuring equipment according to a third embodiment of the present invention.

FIG. 14 is a schematic configuration diagram illustrating the measuring equipment according to a third embodiment of the present invention. In FIG. 14, those elements that are the same as or correspond to those elements in FIG. 14 are indicated by the same reference numerals and duplicate description is omitted.

A basic difference between the present embodiment and the first embodiment is only in that in the first embodiment, the stage 13 adjusts the position of the condensing lens 11 on the optical axis while in the present embodiment the stage 13 adjusts the position of the condensing lens 10 on the optical axis.

In the present embodiment, the control/calculation unit 7 is configured to perform the first to the fifth measuring modes. Instead, the control/calculation unit 7 may be configured to perform respective measuring modes corresponding to the sixth and seventh measuring modes, respectively. In the case of the present embodiment, the condensing lens 11 should be replaced by the condensing lens 10 in the description of the first to seventh measuring modes. In the present embodiment, the standard position of the condensing lens 10 is a position where the rear focal point of the condensing lens 10 coincides with the front focal point of the condensing lens 11.

According to the present embodiment, also a similar advantage to that of the first embodiment can be obtained.

Fourth Embodiment

Figure 15:
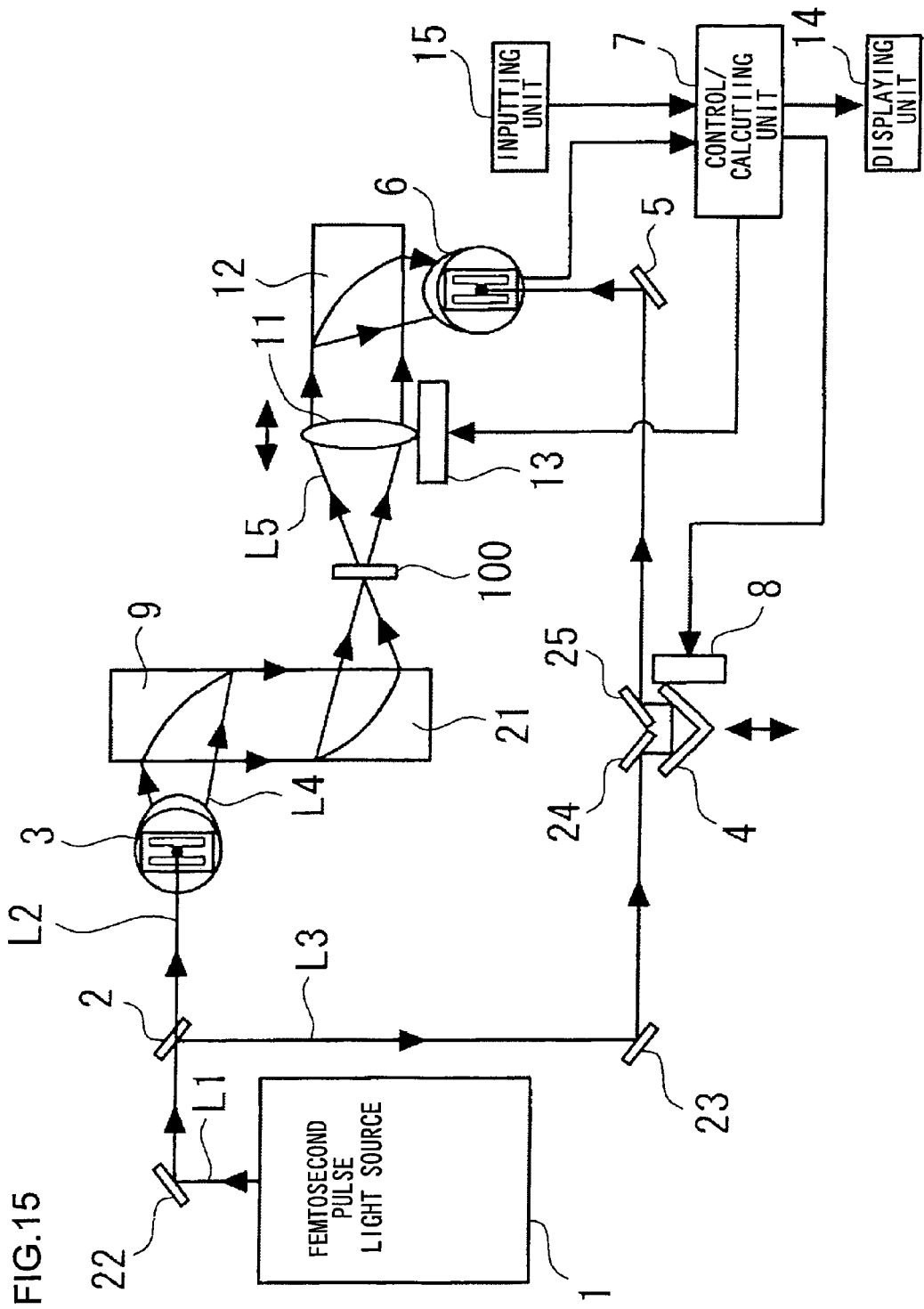
FIG. 15 is a schematic configuration diagram schematically illustrating measuring equipment according to a fourth embodiment of the present invention.

FIG. 15 is a schematic configuration diagram illustrating the measuring equipment according to a fourth embodiment of the present invention. In FIG. 15, those elements that are the same as or correspond to those elements in FIG. 4 are indicated by the same reference numerals and duplicate description is omitted.

A basic difference between the present embodiment and the first embodiment is only in that a parabolic mirror 21 is used instead of the condensing lens 10 and along with this, plane mirrors 22 to 25 are added and each device is arranged as shown in FIG. 15. The parabolic mirror 21 condenses the terahertz pulse light L4 incoming from the parabolic mirror 9 and being converted into a parallel beam. In the present embodiment, the parabolic mirrors 9 and 21 constitute the first condensing optical system that condenses the terahertz pulse light generated by the terahertz light generator 3. The measuring portion for the sample 100 is arranged in the vicinity of the focal point of the parabolic mirror 21.

In the present embodiment, the control/calculation unit 7 is configured to perform the first to the fifth measuring modes.

Instead, the control/calculation unit 7 may be configured to perform respective measuring modes corresponding to the sixth and seventh measuring modes, respectively. In the present embodiment, the standard position of the condensing lens 11 is a position where the front focal point of the condensing lens 11 coincides with the focal point of the parabolic mirror 21.

According to the present embodiment, also a similar advantage to that of the first embodiment can be obtained.

Fifth Embodiment

Figure 16:
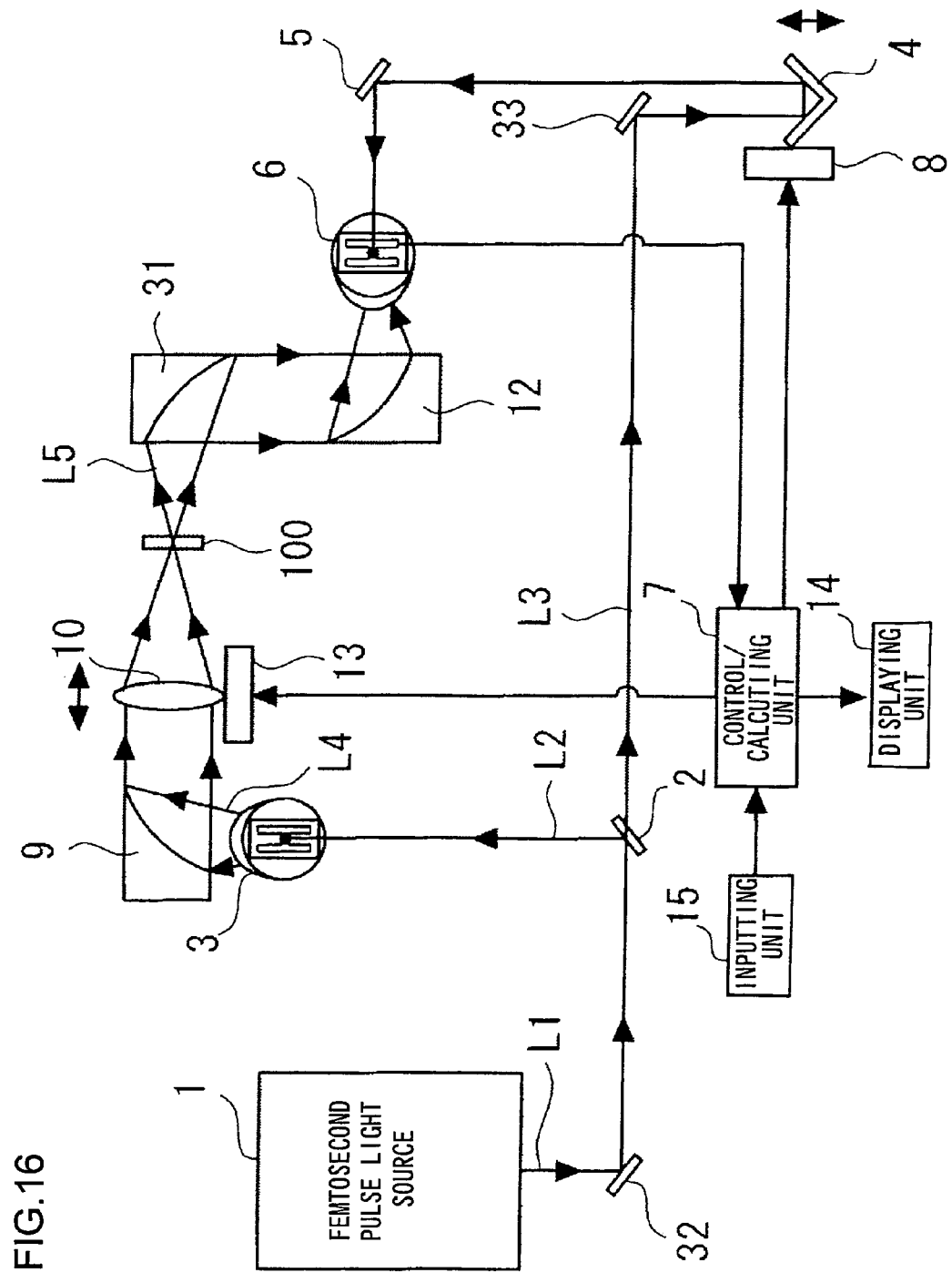
FIG. 16 is a schematic configuration diagram schematically illustrating measuring equipment according to a fifth embodiment of the present invention.

FIG. 16 is a schematic configuration diagram illustrating the measuring equipment according to a fifth embodiment of the present invention. In FIG. 16, those elements that are the same as or correspond to those elements in FIG. 4 are indicated by the same reference numerals and duplicate description is omitted.

Basic differences between the present embodiment and the first embodiment are only in that (i) in the first embodiment, the stage 13 adjusts the position of the condensing lens 11 on the optical axis while in the present embodiment the stage 13 adjusts the position of the condensing lens 10 on the optical axis; and that (ii) a parabolic mirror 31 is used instead of the condensing lens 11 and along with this, plane mirrors 32 and 33 are added and each device is arranged as shown in FIG. 16. In the present embodiment, the parabolic mirror 31 and 12 constitute the second condensing optical system that condenses the terahertz pulse light L5 diverging after being condensed by the first condensing optical system (the parabolic mirror 9 and the condensing lens 10 in the present embodiment) to the terahertz light detector 6.

In the present embodiment, the control/calculation unit 7 is configured to perform each of measuring modes corresponding to the first to the fifth measuring modes, respectively. Instead, the control/calculation unit 7 may be configured to perform respective measuring modes corresponding to the sixth and seventh measuring modes, respectively. In the case of the present embodiment, the condensing lens 11 should be replaced by the condensing lens 10 in the description of the first to seventh measuring modes.

In the present embodiment, the standard position of the condensing lens 10 is a position where the rear focal point of the condensing lens 10 coincides with the front focal point of the parbolic mirror 31.

According to the present embodiment, also a similar advantage to that of the first embodiment can be obtained.

While the present invention has been described above by way of the embodiments, the present invention should not be considered to be limited thereto.

For example, in the first embodiment, a transmissive optical device (for example, a convex lens or a concave lens) having a relatively small positive or negative refractive power may be added between the condensing lens 11 and the arranging position of the sample 100 or between the condensing lens 11 and the parabolic mirror 12, and the transmissive optical device may be adjusted for its position on the optical axis by the stage 13 instead of adjusting the position of the condensing lens 11 on the optical axis by the stage 13.

For example, in the first embodiment, the second condensing optical system may be constituted by an ellipsoidal mirror and a transmissive optical device (for example, a convex lens or a concave lens) having a relatively small positive or negative refractive power instead of the condensing lens 11 and the parabolic mirror 12, and the transmissive optical device may be adjusted for its position on the optical axis by the stage 13 instead of adjusting the position of the condensing lens 11 on the optical axis by the stage 13. On this occasion, for example, the arrangement can be such that the ellipsoidal mirror is arranged so that the first focal point of the ellipsoidal mirror is positioned at a position offset from the rear focal point of the condensing lens 10 on the optical axis, the transmissive optical device is arranged between the first focal point and the ellipsoidal mirror, and the effective light receiving region of the terahertz light detector 6 is arranged at the second focal point of the ellipsoidal mirror.

While the above-mentioned embodiments are each an example of the present invention applied to a time-series converted terahertz spectroscopic equipment, the present invention can also be applied to other terahertz spectroscopic equipment and other measuring equipment using terahertz light.

While an explanation is given above in reference to the embodiments and the examples of variations thereof, the present invention is not limited thereto and other conceivable modes within the technical concept of the present invention are also included by the scope of the present invention.

The disclosure of the following basic application of which the present application claims priority is incorporated herein by reference:

Japanese Patent Application No. 2004-325264 (filed on Nov. 9, 2004).

The invention claimed is:

1. A measuring equipment utilizing terahertz pulse light, comprising:
    a terahertz light generator that generates terahertz pulse light;
    a terahertz light detector that detects terahertz pulse light;
    a first condensing optical system that condenses the terahertz pulse light generated by the terahertz light generator; and
    a second condensing optical system that condenses the terahertz pulse light diverging after being condensed by the first condensing optical system, onto the terahertz light detector, wherein:
    at least one of the first and the second condensing optical systems includes at least one lens having a positive or negative refractive power, the measuring equipment further comprising:
    a position adjusting mechanism that adjusts a position of the at least one lens on an optical axis when the terahertz light detector detects the terahertz pulse light having transmitted through a sample, the sample being arranged in a vicinity of a position of condensing the terahertz pulse light by the first condensing optical system; and
    a controlling unit that controls the position adjusting mechanism to move the position of the at least one lens on the optical axis so that a focused state of the terahertz pulse light having transmitted through the sample to the terahertz light detector is the same as a focused state of the terahertz pulse light to the terahertz light detector when no sample is arranged.

2. The measuring equipment according to claim 1, wherein the controlling unit controls the position adjusting mechanism depending on a thickness and a refractive index of the sample.

3. The measuring equipment according to claim 2 wherein
    the terahertz light generator generates the terahertz pulse light in response to pump pulse light incident to the terahertz light generator;
    the terahertz light detector detects the terahertz pulse light in response to probe pulse light incident to the terahertz light generator; and there is further provided a light path length altering unit that alters a light path length of the pump pulse light and a light path length of the probe pulse light relative to each other.

4. The measuring equipment according to claim 3, further comprising:
   a first time-series waveform obtaining unit that obtains a time-series waveform of electric field intensity of terahertz pulse light incident to the terahertz light detector based on a detected signal from the terahertz light detector, the detected signal being obtained by relatively altering the light path length of the pump pulse light and the light path length of the probe pulse light by the light path length altering unit in a state where the sample is absent;
   a second time-series waveform obtaining unit that obtains a time-series waveform of electric field intensity of terahertz pulse light incident to the terahertz light detector based on a detected signal from the terahertz light detector, the detected signal being obtained by relatively altering the light path length of the pump pulse light and the light path length of the probe pulse light by the light path length altering unit in a state where the sample is arranged in the vicinity of a condensing position at which the terahertz pulse light is condensed by the first condensing optical system; and
   a calculating unit that calculates a moving amount of the at least one lens based on a time difference between a peak of a time-series waveform obtained by the first time-series waveform obtaining unit and a peak of a time-series waveform obtained by the second time-series waveform obtaining unit, wherein
   the controlling unit controlling the position adjusting mechanism based on the moving amount obtained by the calculating unit.

5. The measuring equipment according to claim 3, further comprising:
   a first time-series waveform obtaining unit that obtains a time-series waveform of electric field intensity of terahertz pulse light incident to the terahertz light detector based on a detected signal from the terahertz light detector, the detected signal being obtained by relatively altering the light path length of the pump pulse light and the light path length of the probe pulse light by the light path length altering unit in a state where a reference sample instead of the sample is arranged in the vicinity of a condensing position at which the terahertz pulse light is condensed by the first condensing optical system;
   a second time-series waveform obtaining unit that obtains a time-series waveform of electric field intensity of terahertz pulse light incident to the terahertz light detector based on a detected signal from the terahertz light detector, the detected signal being obtained by relatively altering the light path length of the pump pulse light and the light path length of the probe pulse light by the light path length altering unit in a state where the sample is arranged in the vicinity of a condensing position at which the terahertz pulse light is condensed by the first condensing optical system; and
   a calculating unit that calculates a moving amount of the at least one lens based on a time difference between a peak of a time-series waveform obtained by the first time-series waveform obtaining unit and a peak of a time-series waveform obtained by the second time-series waveform obtaining unit, wherein
   the controlling unit controlling the position adjusting mechanism based on the moving amount obtained by the calculating unit.

6. The measuring equipment according to claim 2, wherein the controlling unit calculates an offset amount between a diverging point of terahertz pulse light that diverges without being transmitted through the sample after being condensed by the first condensing optical system and a diverging point of terahertz pulse light having transmitted through the sample after being condensed by the first condensing optical system and diverging based on a thickness and a refractive index of the sample and controls the position adjusting mechanism based on the calculated offset amount.

7. The measuring equipment according to claim 1, wherein the terahertz light generator generates the terahertz pulse light in response to pump pulse light incident to the terahertz light generator;
   the terahertz light detector detects the terahertz pulse light in response to probe pulse light incident to the terahertz light generator; and
   there is further provided a light path length altering unit that alters a light path length of the pump pulse light and a light path length of the probe pulse light relative to each other.

8. The measuring equipment according to claim 7, wherein the controlling unit
   (i) monitors a detected signal from the terahertz light detector obtained by relatively altering the light path length of the light path of the pump pulse light and the light path length of the light path of the probe pulse light by the light path length altering unit in a state where the sample is arranged in the vicinity of a condensing position at which the terahertz pulse light is condensed by the first condensing optical system, and fixes the light path length of each light path based on the result of the monitoring so that the detected signal becomes maximum;
   (ii) monitors, in the fixed state, a detected signal from the terahertz light detector obtained by moving the lens by the position adjusting mechanism, and controls the position adjusting mechanism so that the lens is positioned at a position at which the detected signal is maximum.

9. The measuring equipment according to claim 1, wherein the controlling unit controls the position adjusting mechanism, so that a rear focal point of the first condensing optical system coincides with a front focal point of the second condensing optical system either when the sample is present or when the sample is absent.

10. The measuring equipment according to claim 1, wherein:
   the controlling unit controls the position adjusting mechanism, so that when the sample is not in the vicinity of the condensing position, the at least one lens is positioned at a first predetermined position, and when the sample is in the vicinity of the condensing position, the at least one lens is positioned at a second position offset from the first position;
   the terahertz light detector detects the terahertz pulse light in a state where the sample is not in the vicinity of the condensing position and in a state where the at least one lens is positioned at the first position to output a first detection result, and detects the terahertz pulse light in a state where the sample is in the vicinity of the condensing position and in as state where the at least one lens is positioned at the second position to output a second detection result; and
   there is further provided a spectroscopic data generating unit that generates spectroscopic data of the sample based on the first and the second detection results.

11. The measuring equipment according to claim 1, wherein the controlling unit controls the position adjusting mechanism, so that when the sample is not in the vicinity of the condensing position, the at least one lens is positioned at a first predetermined position, and when the sample is in the vicinity of the condensing position, the at least one lens is positioned at a second position offset from the first position, and when a reference sample is in the vicinity of the condensing position, the at least one lens is positioned at a third position offset from the first position;

the terahertz light detector detects the terahertz pulse light in a state where the reference sample is in the vicinity of the condensing position and in a state where the at least one lens is positioned at the third position to output a first detection result, and detects the terahertz pulse light in a state where the sample is in the vicinity of the condensing position and in a state where the at least one lens is positioned at the second position to output a second detection result; and wherein the measuring equipment further comprises a spectroscopic data generating unit that generates spectroscopic data of the sample based on the first and the second detection results.

12. The measuring equipment according to claim 1, wherein the controlling unit obtains an offset amount of the second position from the first position based on a thickness and a refractive index of the sample.

13. The measuring equipment according to claim 11, wherein the controlling unit obtains an offset amount of the second position from the first position based on a thickness and a refractive index of the sample and an offset amount of the third position from the first position based on a thickness and a refractive index of the reference sample.

* * * * *